United States Patent
Sciorra et al.

(10) Patent No.: US 7,364,921 B1
(45) Date of Patent: Apr. 29, 2008

(54) METHOD AND APPARATUS FOR SEPARATING BIOLOGICAL MATERIALS AND OTHER SUBSTANCES

(75) Inventors: Leonard Sciorra, Neshanic Station, NJ (US); Joseph Zimnoch, Sellersville, PA (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/869,741

(22) PCT Filed: Jan. 6, 2000

(86) PCT No.: PCT/US00/00274

§ 371 (c)(1),
(2), (4) Date: Jan. 9, 2002

(87) PCT Pub. No.: WO00/40947

PCT Pub. Date: Jul. 13, 2000

Related U.S. Application Data

(60) Provisional application No. 60/114,843, filed on Jan. 6, 1999.

(51) Int. Cl.
*G01N 33/553* (2006.01)
*G01N 33/574* (2006.01)

(52) U.S. Cl. ............ 436/526; 436/518; 436/501; 436/807; 436/824; 435/2; 435/4; 435/7.1; 435/7.2; 435/7.21; 435/7.23; 209/214; 209/222; 210/695; 210/767

(58) Field of Classification Search ........... 436/526, 436/518, 501, 807, 824; 209/214, 222; 210/695, 210/767; 435/2, 4, 7.1, 7.2, 7.21, 7.23
See application file for complete search history.

(56) References Cited

U.S. PATENT DOCUMENTS

| | | | |
|---|---|---|---|
| 4,017,385 A | 4/1977 | Morton et al. | |
| 4,241,176 A | 12/1980 | Avrameas et al. | |
| 4,375,407 A | 3/1983 | Kronick | |
| 4,594,160 A | 6/1986 | Heitmann et al. | |
| 4,772,383 A | 9/1988 | Christensen | |
| 4,935,147 A | 6/1990 | Ullman et al. | |
| 5,004,539 A | 4/1991 | Colwell, Jr. | |
| 5,122,269 A | 6/1992 | De Reuver | |
| 5,137,827 A * | 8/1992 | Mroczkowski et al. | 435/287.2 |
| 5,186,827 A | 2/1993 | Liberti et al. | |
| 5,191,223 A | 3/1993 | Munekata | |
| 5,200,084 A | 4/1993 | Liberti et al. | |
| 5,224,604 A | 7/1993 | Duczmal et al. | |
| 5,236,824 A | 8/1993 | Fujiwara et al. | |
| 5,275,933 A | 1/1994 | Tens et al. | |
| 5,279,936 A | 1/1994 | Vorpahl | |
| 5,336,614 A * | 8/1994 | Brown et al. | 435/397 |
| 5,340,749 A | 8/1994 | Fujiwara et al. | |
| 5,437,987 A | 8/1995 | Teng et al. | |
| 5,466,574 A | 11/1995 | Liberti et al. | |
| 5,508,164 A | 4/1996 | Kausch et al. | |
| 5,536,475 A | 7/1996 | Moubayed et al. | |
| 5,541,072 A | 7/1996 | Wang et al. | |
| 5,543,289 A | 8/1996 | Miltenyi | |
| 5,602,042 A * | 2/1997 | Farber | 436/526 |
| 5,646,001 A * | 7/1997 | Terstappen et al. | 435/7.21 |
| 5,691,208 A | 11/1997 | Miltenyi et al. | |
| 5,770,388 A | 6/1998 | Vorpahl | |
| 5,779,892 A | 7/1998 | Miltenyi et al. | |
| 5,795,470 A | 8/1998 | Wang et al. | |
| 5,876,593 A | 3/1999 | Liberti et al. | |
| 5,939,964 A | 8/1999 | Domigan | |
| 5,993,665 A | 11/1999 | Terstappen | |
| 6,017,719 A * | 1/2000 | Tseng-Law et al. | 435/7.21 |
| 6,638,763 B1 * | 10/2003 | Steindler et al. | 435/368 |

FOREIGN PATENT DOCUMENTS

WO WO 95/14118 6/1995

OTHER PUBLICATIONS

Cheung, M. et al., "*Prenatal diagnosis of sickle cell anaemia and thalassaemia by analysis of fetal cells in maternal blood*", Nature Genetics, vol. 14, 1996, pp. 264-268.
Bier, M. "*Electrophoresis*", Chapter Seventeen, pp. 497-526.

* cited by examiner

*Primary Examiner*—Long V. Le
*Assistant Examiner*—Pensee T. Do
(74) *Attorney, Agent, or Firm*—Licata & Tyrrell PC

(57) ABSTRACT

A method for separating biological materials and other substances is disclosed, wherein a mixture containing desired and undesired components are exposed to magnetic particles having ligands capable of binding to the desired and/or the undesired components to form a magnetic mixture, placing the magnetic mixture onto a substrate material; exposing the substrate coated with the magnetic mixture to a magnetic field of sufficient strength to cause the magnetic components to migrate across the substrate; and repeatedly increasing and decreasing the magnetic field in a pulsing manner with a frequency sufficient to cause the desired magnetic components to separate spatially from the undesired magnetic components. A device for separating biological materials capable of being operated to increase and decrease magnetic field in a pulse fashion is also disclosed.

37 Claims, 15 Drawing Sheets

METHOD AND APPARATUS FOR SEPARATING BIOLOGICAL MATERIALS AND OTHER SUBSTANCES

The present invention relates to a method and apparatus for separating biological materials. Applicants claim the benefit of priority of the filing date 6 Jan. 1999 of U.S. Patent Application 60/114,843, the entire contents of which are incorporated herein by reference.

FIELD OF THE INVENTION

In particular, the present invention is directed to a method for separating biological materials or other substances, comprising the steps of binding a substance of interest to magnetic particles to form a magnetic transfer complex, placing the magnetic transfer complexes onto a support medium, and subjecting the material to pulsed, variable strength magnetic fields which cause the magnetic transfer complexes to migrate across the surface of the support medium. A further embodiment of the present invention is directed to an apparatus capable of creating pulsed, variable strength magnetic fields about a support medium.

In a preferred embodiment of the method of the current invention, highly purified cell sub-populations are isolated from small amounts of heterogeneous cell populations. This embodiment uses magnetic carrier materials which have monoclonal antibodies specific to cell sub-populations which are desired to be separated from the heterogenous population placed on the surface of the magnetic carrier materials. The magnetic carrier materials are introduced to the heterogenous population wherein the magnetic carrier materials bind to the desired cell sub-populations to form magnetic complexes containing members of the desired cell sub-populations. Alternatively, the antibodies on the magnetic carrier materials can be specific to cell sub-populations to be removed from the heterogenous population (leaving the desired cell sub-population), in which case the magnetic complexes contain members of the sub-population to be removed from the heterogenous population.

The heterogenous population, including the magnetic complexes, is then placed in an apparatus according to the current invention. The apparatus comprises a support for a substrate medium which contains the heterogenous population, and a magnetic coil and power supply combination capable of producing pulsed, variable strength magnetic fields around the substrate medium. The heterogenous population is placed in or upon the substrate medium. The heterogenous population is then exposed to a laminar GSR magnetic field, whose direction, strength and duration can be controlled. In this preferred embodiment, the magnetic field is pulsed, rather than constantly applied, about the sample of the heterogenous population. The magnetic complexes then travel through or across the substrate medium and are separated from the remainder of the heterogenous population, because the substrate medium impedes the motion of the unbound materials. The apparatus according to the current invention has the potential to increase quite significantly the specificity and sensitivity ranges now available in currently utilized magnetic bead separating devices.

In a further preferred embodiment the apparatus and method of the current invention is used to separate fetal blood cells from a mixture comprising maternal blood cells and fetal blood cells. The fetal blood cells, once separated by the apparatus and method of the current invention, can be subjected to various tests, as known in the art, to determine, among other properties, the potential for genetic defects in the fetus from which the blood cells originate.

BACKGROUND OF THE INVENTION

The purification of biological materials from uncleared, crude materials or mixtures of materials in a simple, cost effective manner is a great challenge to industry. There are many applications for methods and apparatus which perform such separations, both within the natural and the life sciences. Natural science applications which require purified biological materials include, but are not limited to, the removal of toxic compounds from industrial waste streams, the clean-up of industrial and environmental sites, the detection of contaminants in sewage treatment processes and the like. Among the life science processes which require purified materials are the immunological or other biological assays, biochemical or enzymatic reactions, affinity-based protein purification, DNA/RNA isolation in various molecular biology applications, and cell separations related to cell diagnostics and cell therapeutics.

Separation processes are based on the application of an external force on a mixture, wherein the external force reacts with a property of the components in the mixture. Separation methods can be based on component size (membrane filtration, dialysis, and screening), phase affinity (distillation, chromatography, sublimation, and crystallization), mass (centrifugation and spectrometry) or combinations of properties (gradient transport and electro osmosis).

In one prior art separation method, electrophoresis, an apparatus separates components from a mixture via an electric field. Electrophoresis is the transport of electrically responsive particles in an electric field. Separation is based on different rates of migration of the components through a solution under the influences of an electric field. Particles in a solution create their own ionic environment, hence they create their own electrical field. The electric field of the apparatus causes the components to migrate by interacting with the electrical fields created by the components.

In many molecules, in particular proteins and macromolecules, charge originates from the ionization of functional groups in the molecules. These charged molecules tend to adsorb oppositely charged particles near the phase boundary between the molecule and the solution in which it is placed. This collection of charged particles and the ions adsorbed thereon is referred to as the electrical double layer. The electrical double layer is often larger in size and has a higher charge density than the original particles.

The electrical double layer creates an electric field about the particle. The potential at the surface of the electric double layer, $\psi_O$, is defined as $Q/(\in a)$, where Q is the resultant charge on the electric double layer, $\in$ is the dielectric constant of the solution and a is the radius of the electrical double layer. This potential of this electric field decreases with distance x according to $$\psi_x = \psi_O \exp(-\kappa X)$$

where $\psi_O$ is the value of the potential of the electric field at the surface of the electrical double layer and $\kappa$ is the Debye-Huckel constant $$\kappa = (8\pi e^2 n_o z^2 / \in kT)^{1/2}.$$

By definition e is the electronic charge, $n_o$ is the bulk concentration of each ionic species, z is the valence of the symmetrical electrolyte, T is the absolute temperature and k is the Boltzmann constant.

Upon application of an external electric field to the solution, the particles, including the electric double layer, are subjected to four forces: the electrophoretic attraction $K_1$, the Stokes friction $k_2$, the electrophoretic retardation $K_3$, and the relaxation effect $K_4$.

$K_1$=QE (the product of the charge of the particle and the potential gradient);

$K_2$=$-f_cU$ (the product of the electrophoretic velocity, U, and the coefficient of friction of the particle $-f_e$, defined as 6πηa, where η is the viscosity of the solvent);

$K_3$=(∈ζa-Q)E (where ζ is the electrokinetic potential, the electric potential ψ at the shear boundary of the particle).

At equilibrium with the electric field, the sum of these four forces is zero, and the resulting electrophoretic velocity U becomes $$U=(QE+K_3+K_4)/f_c.$$

By ignoring the relaxation effect, the electrophoretic mobility μ is determined as the ratio of the velocity over field strength.

$$\mu=U/E=(\delta\zeta)/(6\pi\eta).$$

As a result the ability of particles to be separated by electrophoresis can be determined from knowledge of the intrinsic properties of the solution and the particles in the solution. Different types of particles will travel through the same solution, while being subjected to the same electric field, at different rates. This rate differentials allow for component separation.

The resolution provided by the rate differential is enhanced if an element of discontinuity is introduced into the electric field. For example, the mixture could be subjected to a pH gradient, the sieving effect of high density gels, or the adherence of one of the substances in the mixture to a supporting medium. Other factors include shape of the separation vessel and gravimetric effects introduced by running the separation in a vertical direction.

Magnetophoresis is the transport of magnetically responsive particles in a magnetic field. A solenoid carrying current generates a magnetic field inside the core of the solenoid which is parallel to the axis of the solenoid. A ferromagnetic core in one half side of the solenoid will generate a magnetic field with the same configuration extending the magnetic field of the pole linearly to the end of the solenoid. The force acting on a particle as a result of the magnetic field is given by $$F=m\cdot B$$

here m is the magnetic pulse strength of the particle, and B is the flux density (strength) of the magnetic field. Separation is based on different rates of migration of the components through a solution under the influence of the magnetic field. The magnetic field generated by the solenoid causes responsive particles in the solution to become induced magnets, thereby creating their own magnetic field. These particles can be considered to be microscopic magnets. The magnetic field of the apparatus causes the components to migrate by interacting with the magnetic fields created by the components. In magnetophoretic separation devices and methods, the separating force (supplied by the action of an external electric field on the electrical fields of the electrical double layer in electrophoretic devices and methods) is replaced by the action of an external magnetic field on particles exhibiting their own magnetic fields. The components desired to be removed via magnetophoretic devices and methods either exhibit magnetic fields of their own accord or by the attachment thereto of a magnetic particle. Such particles may be iron particles which exhibit magnetic fields by magnetic induction. The components to remain in solution either exhibit no magnetic field or exhibit a weaker magnetic field and decreased transport properties than that of the desired component.

In the case where none of the components in the solution exhibits its own magnetic field, magnetic particles (with an affinity for the component desired to be separated from the solution) are introduced into the solution. The affinity of the magnetic particles is often the product of having substances (which bind to the component desired to be separated from the solution with greater affinity than for any other components in the solution) placed on the surface of the magnetic particles. The magnetic particles then bind to the component desired to be removed. The usefulness of magnetic particles which have a biological affinity for a substance desired to be removed in such purification processes is well known in the art.

After reactions occur between the substance on the magnetic particle surfaces and the desired component, the particles, with the component bound thereto, are magnetically separated from the solution. The separation from the solution occurs by applying a magnetic field to the solution, thereby causing the magnetic particles, with the component bound thereto, to be transported through the solution toward the point of greatest (external) magnetic field strength. The other components of the solution, having no, or a lesser, magnetic susceptibility are not transported through the solution by the magnetic field. After the magnetic particles, with the component bound thereto, are removed from the solution, the particle-bound component can be recovered from the magnetic particles by methods known in the art for cleaving the bond between component and substance.

A problem exists in the art when one desires to separate components which do not exhibit magnetic fields of their own accord that are significantly different, one from the other in terms of strength and intensity, to allow separation of the components based on the reaction of their own inherent magnetic fields to the external magnetic field. This problem is further exacerbated when the components desired to be separated are of a similar nature in terms of the types of particles which bind thereto. In such instances it is difficult, if not impossible, to produce a magnetic particle with a substance on its surface which will bind to one of the components and not the other. Hence, there is no way to have the components exhibit magnetic fields that are sufficiently different to react differently in response to an external magnetic field, thus allowing the external magnetic field to separate the components. Such a situation arises when one attempts to separate fetal red blood cells from maternal whole blood. As understood herein, "fetal red blood cells" means nucleated fetal red blood cells.

It is desired to obtain a purified sample of fetal blood cells during the gestation period of the fetus. Fetal cells are used to obtain a wealth of information about the gestating fetus. Fetal nucleated blood cells can be used as a source of DNA to determine the fetus gender, and to predict the likelihood of the occurrence of such genetic defects as Down's syndrome, P-thalassemia, phenylketonuria, cystic fibrosis, Duchene's muscular dystrophy, sickle cell anemia, and the like. Known methods of obtaining a purified sample of fetal blood cells, such as taking a periumbilical blood sample (PUBS) expose the fetus to an extremely high risk of injury, and could cause abortion of the fetus. Even amniocentesis, which comprises removing amniotic fluid from the amniotic sac, exposes the fetus to some risk of injury.

It is known in the art that fetal red blood cells are present in the maternal whole blood supply as early as fifteen weeks into the gestation period. Therefore, maternal blood could be a source of fetal red blood cells. Drawing blood from the mother to obtain the supply of fetal red blood cells greatly reduces the risks associated with removing amniotic fluid from the placenta. Hence, it is desirable to develop a method and apparatus for purifying the fetal cell sub-population from the maternal blood sample. The desired method should obtain a high degree of purity while being minimally invasive to the mother and fetus. This would allow the performance of the useful tests on the fetal cells without the risks attendant with the removal of amniotic fluid.

Current devices and methods of separating biological materials, especially those that attempt to separate fetal cells from the maternal blood, are known in the art. All known devices and methods suffer from major drawbacks, among which are 1) the extremely low yield of fetal cells recovered for analysis, 2) the large quantity of maternal blood that is taken, and 3) the large amount of maternal cell contamination that is seen in the fetal blood cell sample, even after the final purification step. Moreover, none of the known devices and methods use the, pulsed, variable strength magnetic fields of the apparatus and method of the current invention.

Magnetic Activated Cell Sorting (MACS) binds small iron beads covered with a monoclonal antibody, specific for the component desired to be removed from the solution. The beads are introduced into the solution, where the antibodies react with the component to be removed, binding the beads to the component. The solution is then applied to a magnetized surface. The magnetic surface attracts the magnetic particles, thereby attracting the component bound thereto. The surface is then washed to remove the non-bead-coated cells. However, when separating fetal blood cells from a maternal blood supply, it has proven difficult to effectively attach iron beads to internal cellular markers on the fetal blood cells (such as fetal hemoglobin). As a result, to date, MACS has failed to provide the high level of separation achieved by the current invention. MACS suffers from non-specific adhesion of components to the metal filings and difficulty in removing magnetized components from the metal filings.

Even in instances where MACS has been performed using surface antigenic markers like CD 71, inherent difficulties in the MACS procedure prevent achieving the high yield and purity from minimal samples as achieved by the current invention. MACS requires a large initial sample to attain appreciable yields of the desired cell sub-population removed from the original sample. The MACS apparatus creates areas having insufficient magnetic field strength to remove the desired sub-population from the sample. Moreover, even when the desired sub-population particles are bound to the MACS apparatus, a large number of washing steps are required to remove the bound cells from the magnetic surface. These washing steps not only decrease the yield of the desired sub-population, but decrease the concentration of the desired sub-population present in the washing step effluent.

Fluorescent Activated Cell Sorting (FACS), an enrichment procedure, uses lasers to excite cells labeled with specific monoclonal antibodies as an enrichment means. These labeled cells are then sorted for further analysis. This labeling method allows one skilled in the art to realize the presence of the desired component in solution, but does nothing to separate the desired component from the solution. Either before of after labeling, the desired substance is removed by other means.

FACS is generally preceded by sieving the maternal blood sample to a discontinuous gradient to form a layer rich in nucleated red blood cells (NRBC). This NRBC layer is then further purified by panning to remove CD 45+ cells (seen on almost all lymphocyte lineage cells, but not seen on NRBC). Markers comprising fluorescently labeled monoclonal antibody are then attached to the remaining cells. Currently, the two markers with the best fetal cell specificity have been monoclonal antibody to the CD 71+ surface antigen and monoclonal antibody to the internal gamma chain of fetal hemoglobin. The fluorescent labeling of the NRBC makes them identifiable for separation from the maternal blood supply by micro manipulators. (Bianchi, 1995).

Cheung et. al. (1996) attempt to isolate fetal cells present in the maternal circulation for genetic screening to search for molecular defects. The method of Cheung et al. comprises the steps of density gradient separation of the maternal blood supply, subjecting the fetal cell enriched layer to MACS utilizing a CD71-binding particle, applying the enriched portion from the MACS to a support, staining with antibodies specific for fetal or embryonic hemoglobin, and removing stained fetal cells with micro-manipulators.

U.S. Pat. No. 4,241,176 to Avrameas et al. discloses a magnetic gel for use in separating materials. Optionally the gel can contain an antibody specific to the material which is desired to be separated from a solution. The magnetic gel is placed along the inside walls of a column and held in place by a static magnetic field, as opposed to the current invention which uses pulsed, variable strength magnetic fields.

U.S. Pat. No. 4,375,407 to Kronick discloses a high gradient magnetic separation device having a filamentary magnetic material in the interior chamber thereof. This reference discloses coating the filamentary material with a coating of hydrogel polymer. The device disclosed in this reference uses uniform magnetic fields. There is no teaching of the use of the pulsed, variable strength magnetic fields of the current invention.

U.S. Pat. No. 4,594,160 to Heitmann et al. discloses a magnetic separator having a combination of screens and balls placed in the interior chamber thereof to intensify the magnetic field strength within the chamber. The separator uses direct-current to produce a magnetic field of at least $1.5 \times 10^5 H$ at all times. Therefore, there is no teaching of pulsing the strength of the magnetic field, as utilized in the current invention.

U.S. Pat. No. 4,772,383 to Christensen also discloses a high gradient magnetic separator having permanent magnetic devices generating strong magnetic fields across a separating chamber, as opposed to the pulsed, variable strength magnetic fields utilized by the current invention.

U.S. Pat. No. 5,004,539 to Colwell et al. discloses a magnetic separator having permanent magnetic elements which cause the separation chamber to be subjected to a permanent magnetic field. The magnetic flux return paths are made of ferromagnetic materials (column 3, lines 13-16), which by definition, permanently maintain their magnetic state. As such, the magnetic flux channels of the separator disclosed in this reference are incapable of producing the pulsed, variable strength magnetic fields utilized by the current invention.

U.S. Pat. No. 5,122,269 to De Reuver discloses a magnetic filter wherein the magnetic gradient across the filter chamber is substantially constant. The substantially constant magnetic gradient is required to maintain even filling, and reduced emptying, of the filter. There is no teaching of using a pulsed, variable strength magnetic field as utilized in the current invention.

U.S. Pat. No. 5,186,827 to Liberti et al. discloses a device and method for separating biological materials using magnets to produce magnetic fields about a contact surface. The magnetic flux density quickly reduces in a direction away from the surface, thereby allowing the device to collect the desired biological component in a thin layer on the contact surface, preventing the undesired component from becoming entrapped in the desired material layer. There is no teaching of the benefits of a pulsed, variable strength magnetic field as utilized in the current invention.

U.S. Pat. No. 5,200,084 to Liberti et al. discloses a method and apparatus for magnetically separating biological materials comprising a magnetic field producing element surrounding a chamber which contains magnetic field gradient intensifying means in the form of iron mesh or wires. The desired material is collected on the surface of the magnetic field gradient intensifying means. There is no teaching of the benefits of a pulsed, variable strength magnetic field as utilized in the current invention.

U.S. Pat. No. 5,236,824 to Fujiwara et al. discloses an apparatus and method for quantitating the amounts of biological materials separated by high gradient magnetic separation. After separation, a light source, preferably a laser light, is radiated upon the separated material and the amount of returned (scattered, reflected) light is measured to determine the quantity of material separated. There is no teaching of the benefits of a pulsed, variable strength magnetic field as utilized in the current invention.

U.S. Pat. No. 5,275,933, to Teng et al. discloses material separation via a discontinuous gradient. Test tubes are filled with three HISTOPAQUE solutions of different densities to provide a triple gradient layer in each of the tubes. Whole maternal blood is added to the top of this triple gradient and the tubes are spun to yield layers into which cells of different densities have been partitioned. The top layer is rich in lymphocytes. The second layer contains NRBCs and the third layer is predominantly populated with granulocytes. As noted at column 6, line 66 through column 7, line 5, the fetal cells are spread about over different layers in the test tube after centrifugation, not in a single discreet layer allowing for easy removal and analysis of the fetal cells. Morever, the number of fetal cells yielded in this method is quite low and varies between different pregnant woman (between 1/10,000 to less than 1/1,000,000). Further, there is no teaching of the benefits of a pulsed, variable strength magnetic field as utilized in the current invention.

U.S. Pat. No. 5,279,936 to Vorpahl discloses a method of magnetically separating materials in solution. The materials desired to be separated are bound to magnetic carriers. A second solution, of different density than the material-containing solution is contacted with, without mixing, the material-containing solution. The two fluid system is then subjected to static magnetic fields and the material bound to the carrier migrates across the solution interface. There is no teaching of the benefits of a pulsed, variable strength magnetic field as utilized in the current invention.

U.S. Pat. No. 5,340,749 to Fujiwara et al. discloses a method for collecting specimens comprising labeling the specimens with magnetic particles and subjecting the labeled particles to a permanent gradient magnetic field. There is no teaching of the benefits of a pulsed, variable strength magnetic field as utilized in the current invention.

U.S. Pat. No. 5,437,987 to Teng et al. (Inventor's name misspelled as "Tens" on the cover page of the patent), is a continuation-in-part of the application which matured into U.S. Pat. No. 5,275,933. The non-magnetophoretic method disclosed in this reference uses a "panning" step after the gradient separation process. After gradient separation, the layer which contains the fetal NRBCs is washed and suspended in a physiologic solution. The solution is then applied to a substrate which has bound thereto cold agglutinin (IgM) antibodies with anti "i" specificity. This antibody binds to an epitope on the fetal NRBCs (made from repeating N-acetyl lactosamine units of a given structure), thereby attaching at least a portion of the fetal NRBCs to the substrate. Non-adherent cells are then washed from the substrate. There is no teaching of the benefits of a pulsed, variable strength magnetic field as utilized in the current invention.

U.S. Pat. No. 5,466,574 to Liberti et al. is a continuation-in-part of the application which matured into U.S. Pat. No. 5,186,827. This magnetic flux density of the device disclosed in this reference quickly reduces in a direction away from the surface, thereby allowing the device to collect the desired biological component in a thin layer on the contact surface, preventing the undesired component from becoming entrapped in the desired material layer. The preferred magnetic field generating means are permanent magnets the field strength of which is enhanced through the placement of ferromagnetic materials (permanently magnetized, by definition) in the chamber of the device. There is no teaching of the benefits of a pulsed, variable strength magnetic field as utilized in the current invention.

U.S. Pat. No. 5,639,669 to Ledley discloses a device and method for separating maternal blood cells and fetal blood cells from a mixture comprising the two. The device and method disclosed by Ledley uses ultrasonic mixing to enhance the separation. Although Ledley's method applies an electromagnetic field to a treated sample containing maternal and fetal blood cells, Ledley's method and apparatus differ from those of the current invention. The Ledley method and apparatus do not utilize a pulsed, variable strength magnetic field as utilized in the current invention.

Moreover, Ledley's device and method require manipulation of an extensively pre-treated solution containing the maternal and fetal blood cells to achieve appropriate conditions of $O_2$ concentration, pH, $Cl^-$ ion concentration, $CO_2$ concentration and temperature of the solution. Once the optimal conditions are finally reached, the solution is subjected to a magnetic field. To prevent conglomeration of the maternal and fetal blood cells, Ledley utilizes ultrasonic vibrations to aid in the separation process.

International patent Publication No. WO 95/14118 to Shih et al. discloses a method for separating biological materials by electrophoresis using a gellable polymeric material. There is no teaching of a the benefits associated with using a pulsed, variable strength magnetic field to separate biological materials, as utilized in the current invention.

SUMMARY OF THE INVENTION

An apparatus and method for separating biological materials and other substances has been invented. The apparatus and method provide highly purified substances, in acceptable yields, from a sample containing the desired substance. In a preferred embodiment, the invention comprises a pulsed, laminar magnetic field cell transport apparatus and a pulsed, laminar magnetic field separation method capable of isolating highly purified cell sub-populations from small amounts of heterogeneous cell populations. One method according to the current invention uses magnetic particles which incorporate biological ligands, in particular monoclonal antibodies, which bind to the specific antigenic cell markers on the cells desired to be removed from the heterogenous population. More than one type of the magnetic particle, each type having a different ligand, may be used to remove one or more desired cell type. The heterogenous population containing the cells (attached to the magnetic particles) is then placed on a substrate medium. When placed in the apparatus of the current invention, the heterogenous population is exposed to laminar magnetic fields, whose direction, strength and duration can be controlled. The desired cells then travel through or across the medium and are separated from cells not attached to magnetic particles in the heterogenous population. Additionally, it is possible that each magnetic particle may bind to more than one cell, transporting more than one cell with the movement of each magnetic particle. Under the appropriate conditions, subsets of magnetic particle-carrying cells can also be separated from the solution. This further level of separation may be a function of cell isotypes having a different number of antigenic surface markers on their surface. This difference in the number of antigenic surface markers causes a different amount of particles to bind to the surface of the cell isotypes, thereby increasing the effect of the magnetic fields generated by the apparatus of the current invention on the cells having the particles bound thereto. The current invention has the potential to increase quite significantly the specificity and sensitivity ranges now available in currently utilized magnetic bead separating devices.

It is an object of the current invention to provide a method for separating biological materials or other target substances from a mixture contain the target substances and other undesired components.

It is a further object of the invention to provide a method for separating biological materials and other substances from a mixture containing desired and undesired components comprising placing a sample of said mixture onto a substrate material; exposing said substrate coated with said sample to a magnetic field of sufficient strength to cause the desired components to migrate across said substrate; and repeatedly activating and deactivating said magnetic field in a pulsing manner with a frequency sufficient to cause said desired magnetic components to separate spatially from the undesired components.

It is a further object of the invention to provide a method for growing one or more components of the mixture on the substrate material. Preferably, one or more of the separated materials is grown on the substrate material.

It is a further object of the invention to provide a device for separating biological materials or other substances, which is capable of being operated to activate and deactivate a magnetic field in a pulsing manner.

Other objects and advantages of the current invention will become apparent to those skilled in the art from the accompanying description of the current invention.

DETAILED DESCRIPTION OF THE INVENTION

The preferred embodiments of the invention will now be described, with reference to the drawings. All patent applications, patents, and literature references cited in this specification are hereby incorporated by reference in their entirety.

Figure 1:
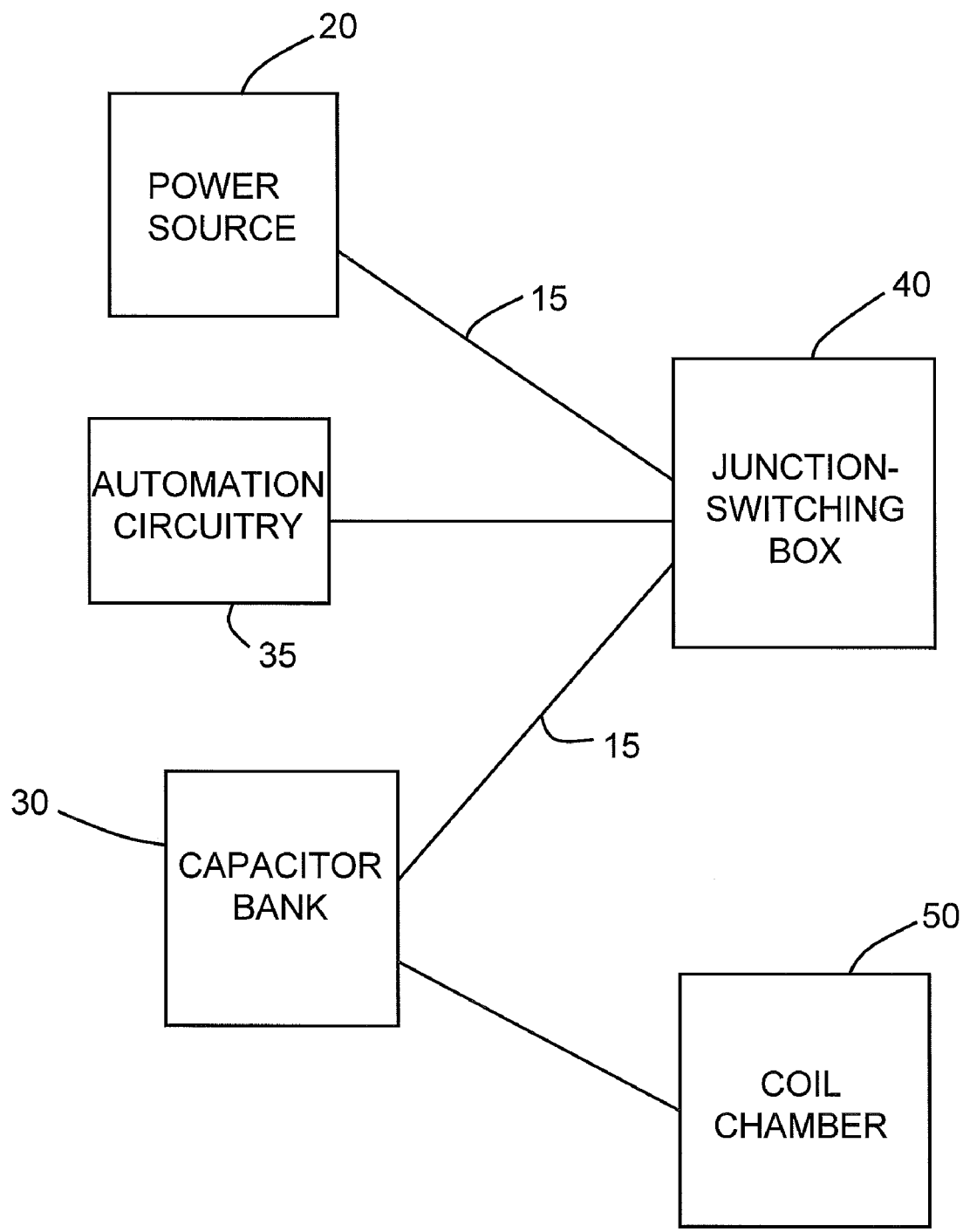
FIG. 1 is a block diagram of the components of the pulsed, laminar magnetic field transport system of the invention.

As illustrated in FIG. 1, the apparatus 10 according to the current invention generates a pulsed magnetic field by the discharge of capacitors 31 which transmit a transient electric current through coil 57. The apparatus comprises a power source 20, a bank of capacitors 30, a switching/junction box 40, and a coil chamber 50. The power source 20, capacitor bank 30, switching/junction box 40, and coil chamber 50 may all be contained in a single housing unit (not pictured).

The variable output voltage of the power source 20 should convert standard alternating electrical current (AC) to a direct current source (DC) for charging the capacitor bank 30 and should be compatible with the voltage rating of the capacitor bank 30. The variable output voltage of the power source 20 should further have a sufficient rating to maintain the charging time of the capacitor bank 30 to less than 10 seconds. The power, current, and voltage output levels of the power source 20 can be controlled by the user of the apparatus. Preferred power sources deliver an electromotive force of between about 5 and about 50 Volts to the capacitor bank 30 (as used herein, the term "about" means within a margin of commonly acceptable error for the determination being made, using standard methods). The current and voltage output levels of power source 20 should be variably controllable by the user of the apparatus of the invention, either manually or through the operation of automated circuits 35.

The maximum current flows when the capacitance of the capacitors 31 and the inductance and resistance of the coil 57 have the following characteristics: $R=2\sqrt{(L/C)}$, where $R=4\Omega$, $L=275$ mH, and $C=0.07$ F (in series arrangement). The automated circuits 35 can be programmed as known in the art to operate without constant user supervision. Typical power supplies are readily available from a commercial supplier. An example of a suitable power supply is the Sola Copper Line series.

The power from power source 20 is fed to capacitor bank 30 through power cable 15. The power cable 15 should be rated to carry a current of 20 amps over a length of 20 feet. A preferred power cable 15 is an AWG #12 cable. The capacitor bank 30 comprises a plurality of capacitors 31. The means used for placement of the capacitors 31 are unimportant, as long a proper cooling is allowed about the capacitors. In one embodiment, the capacitors could be stored in a substantially upright position, with the major axes of the generally cylindrical bodies of the capacitors 31 in a substantially vertical position.

Figure 2:
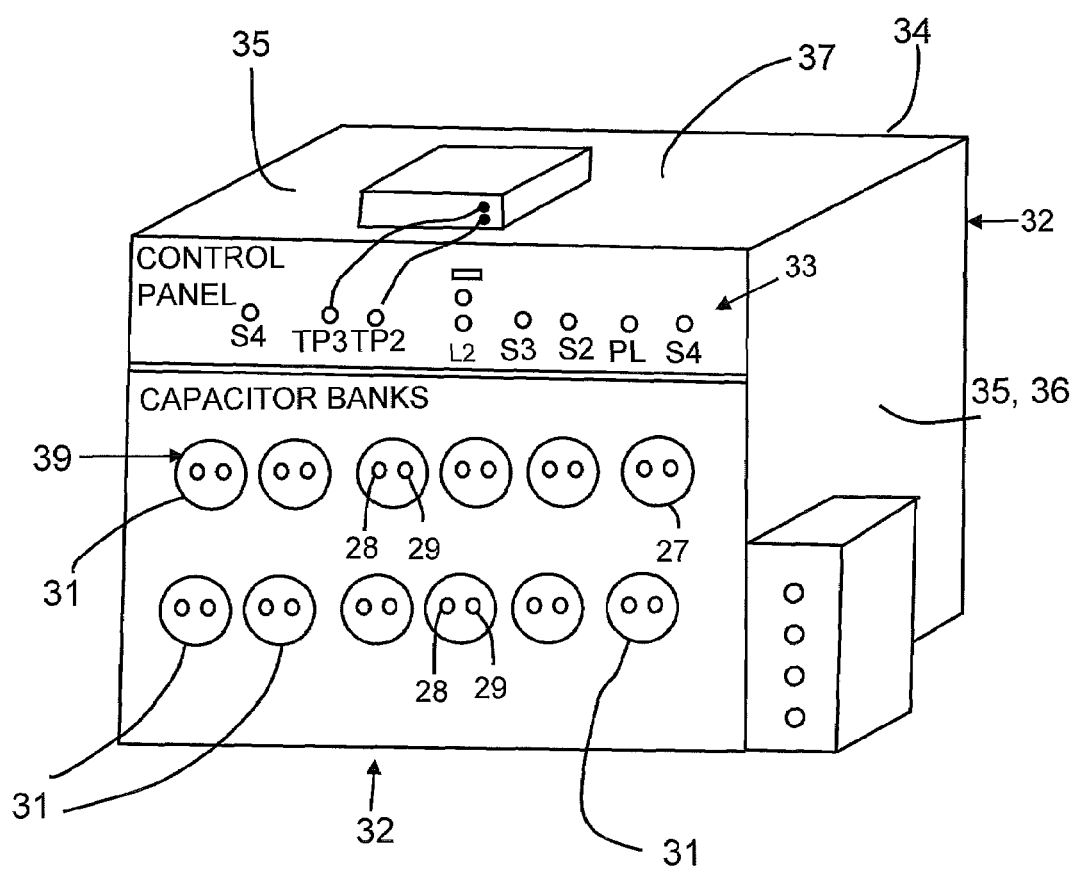
FIG. 2 is a perspective view of a cabinet for the capacitor bank of the device of the invention

FIG. 2 illustrates an embodiment wherein capacitors 31 are stored in a cabinet 32. Cabinet 32 stores capacitors 31 in a position wherein the major axes of the generally cylindrical bodies of the capacitors 31 are in a substantially horizontal position. Regardless of their orientation, the capacitors 31 is preferably stored in a manner that allows ease of access to the anode 28 and cathodes 29 of the capacitors 31 and prevents movement of the capacitors 31, although movement of the capacitors 31 should not affect their performance. Cabinet 32 comprises a front panel 33 and rear panel 34 with support means 35 attaching the front panel 33 to rear panel 34. In the embodiment of the cabinet illustrated in FIG. 2, the support means 35 are side panels 36 and top and bottom panels 37, 38. However, the support means 35 could also comprise a plurality of spacers of equal length placed between front panel 33 and rear panel 34, as long as such spacers provide necessary support for cabinet 32 to allow cabinet 32 to stably support the capacitors 31 when placed in cabinet 32. Front panel 33, rear panel 34, and support means 35 could be prepared from any material known in the art that would support the cabinet 32 and the capacitors 31 stored therein. Non-limiting examples include, wood, sheet metal, ABS plastics, and the like.

Front panel 33 has placed therein a plurality of openings 39 of sufficient size to allow passage of at least individual capacitors 31 there through. Front panel 33 should have sufficient opening spaces 39 to allow storage in cabinet 32 of as many capacitors 31 as are desired. Capacitors 31 are placed in cabinet 32 in a position allowing easy access to the anode 28 and cathode 29 of capacitors 31. In embodiments wherein rear panel 34 has no openings placed therein to allow the opposite end of the capacitors 31 (the end not having the anode 28 or cathode 29 thereon) to rest thereagainst when capacitors 31 are placed in cabinet 32, capacitors 31 are maintained in position (wherein the major axes of the generally cylindrical bodies of the capacitors 31 are substantially horizontal) by cradles 27. Cradles 27 may also be used in those embodiments wherein the rear panel 34 has openings through which the opposite ends of capacitors 31 pass.

Cabinet 32 may be structured to have the anodes 28 and cathodes 29 exposed, or cabinet can have a cover or be placed inside an external enclosure.

Figure 3:
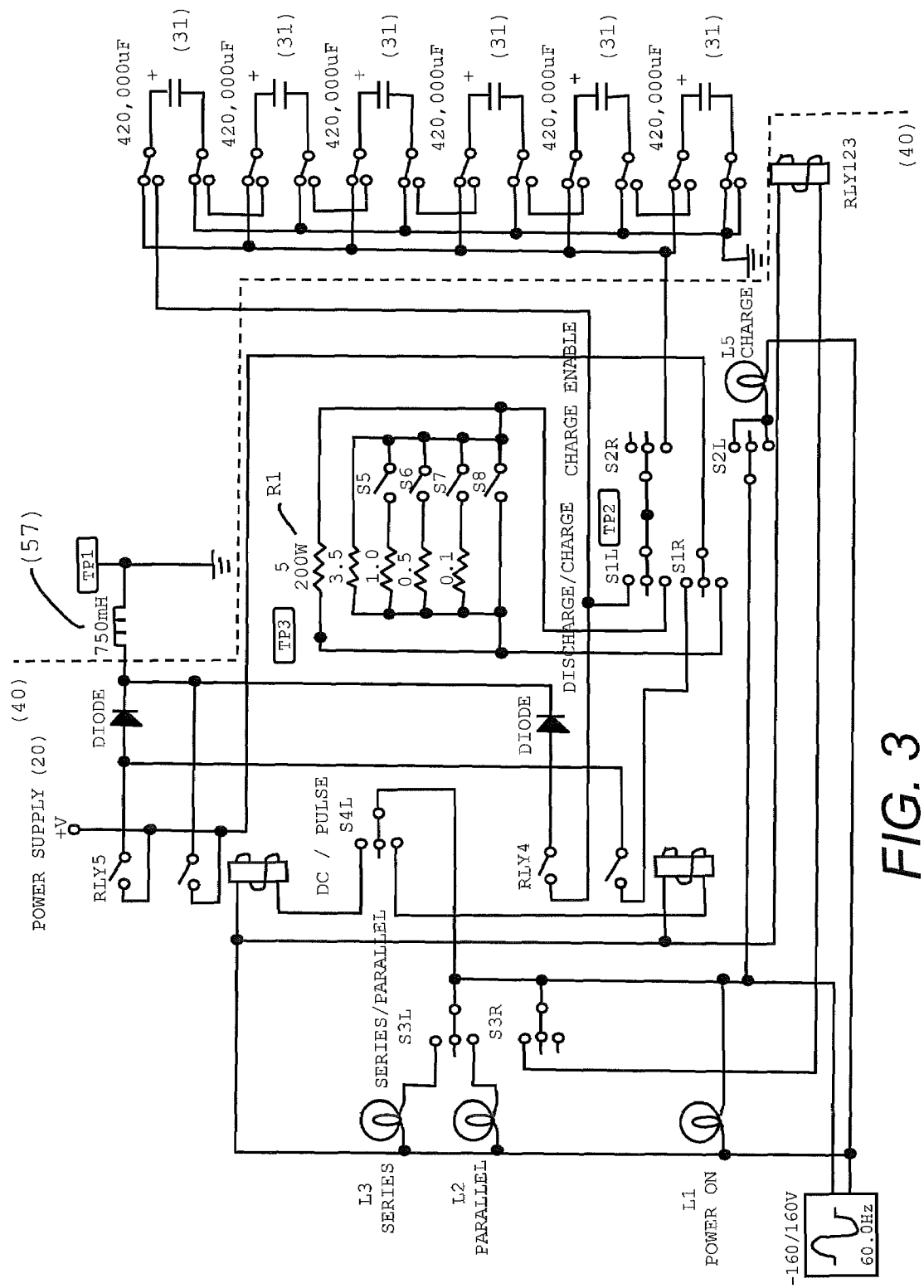
FIG. 3 is a schematic showing the wiring of the power source, capacitor bank, switching/junction box and coil chamber of a first embodiment of the device of the invention.

A first preferred embodiment for wiring the connections of the device of the current invention, including power source 20, capacitors 31, junction-switching box 40, and winding coil 57 is illustrated in FIG. 3. Preferably capacitors 31 comprise a bank of at least six individual capacitors, more preferably twelve individual capacitors. Preferably the individual capacitors have a voltage of about 40 volts each and a capacitance of about 420,000 µF each for use with a winding coil 57 having at least about 20,000 ampere•turns. Junction-switching box 40 comprises a circuit of resistors, switches and diodes, as pictured in FIG. 3. The circuit of junction-switching box 40 allows the capacitors 31 to be charged in parallel (to facilitate rapid charging) and discharged in series (to facilitate maximum acceleration of current flow through the winding coil 57). In the embodiment pictured in FIG. 3, junction-switching box 40 comprises resistors having values of about 5, 3.5, 1.0, 0.5, and 0.1 ohm.

The control panel of junction-switching box 40 has four control switches for operator control, FIGS. 2 and 3. The switches can be controlled manually or via automated or programmed operation. The switches are spring loaded and can be mounted on the front panel of the junction-switching box 40 for easy access to the operator of the device, when manually operated. Each switch has three positions. In the middle position all switches are open. When switch S1 is placed in the down position, the DC voltage from the power source 20 is connected to the surge resistor R1 which is in parallel with the resistors of the time charge control circuits. The output of surge resistor R1 is connected to switch S2. When switch S2 is in the down position, the DC voltage is connected to the capacitors in parallel. Switch S3 in the down position lights lamp L2. Test Terminal TP2 measures the voltage on the capacitors 31 in parallel or in series. Test Terminal TP1 is system ground. With switches S1, S2, and S3 in the down position the capacitors are charged by the power source 20. With switches S1, S2, and S3 in the up position, the capacitors are in series configuration (240 V), and are connected to the output relay RLY4. S4 in the down position completes the circuit, allowing the 240 Volts charged on the series capacitors 31 to be released to the coil chamber 50 for the pulsed, laminar magnetic fields. RLY5 connects power source 20 to coil 57 providing a DC bias voltage to coil 57. Preferably coil 57 remains energized via power source 20 when the capacitors 31 are not energizing the coil 57. More preferably, power source 20 constantly energizes coil 57. The 120 V, 60 Hz power supply operates the relays.

Figure 4:
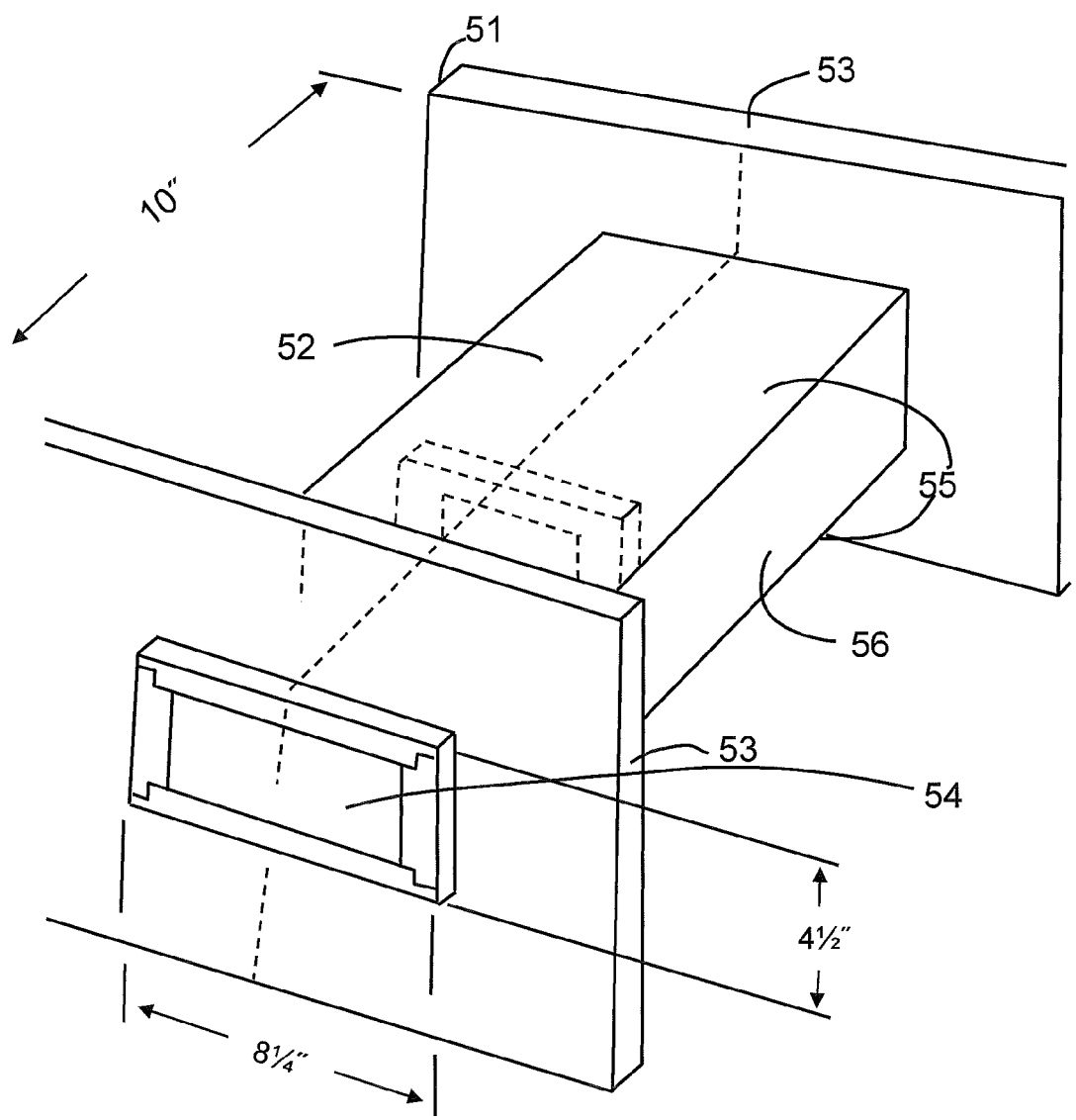
FIG. 4 is a perspective view of a first embodiment of the winding core of the coil chamber of the device of the invention.

FIG. 4 illustrates a first embodiment of a winding core 51 of the current invention. Winding core 51 comprises a central tube 52 and end braces 53. Central tube 52 is an elongate structure with a port 54 on either end thereof. Central tube 52 provides the chamber wherein the support base 60 (not shown) is placed. Central tube 52 can be of any shape that permits generation of a laminar magnetic field of uniform density and will allow insertion of support base 60 into the interior thereof and placement of winding coil 57 (not shown) on the exterior thereof. Preferably central tube 52 has a cross-sectional shape that is rectangular. As illustrated, central tube 52 comprises generally rectangular upper and lower panels 55 continuously joined to side panels 56.

Preferably upper and lower panels have dimensions of about 10 inches by about 8.25 inches, and side panels have dimensions of about 10 inches by abut 4.5 inches. These dimensions create ports of about 4.5 by about 8.25 inches. Winding core 51 can be manufactured from any non-magnetic material, strong enough to support the weight of the winding coil 57, and which does not interfere with the concentration of the magnetic field generated inside the central tube 52 by winding coil 57. Examples of such materials are polyethylene, glass, ABS plastic and wood.

Figure 5A:
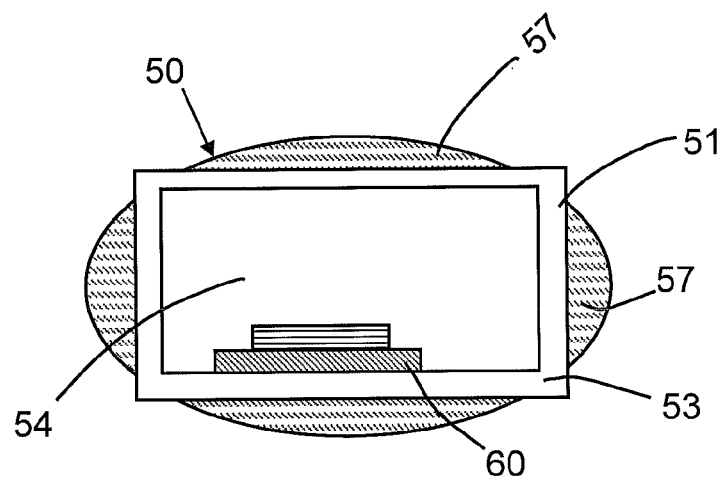
FIG. 5 A is a front view of the coil chamber of the invention.
FIG. 5B is a side view of the coil chamber of the invention.
FIG. 5C is a top view of the platform, showing the substrate base in place.
Figure 5B:
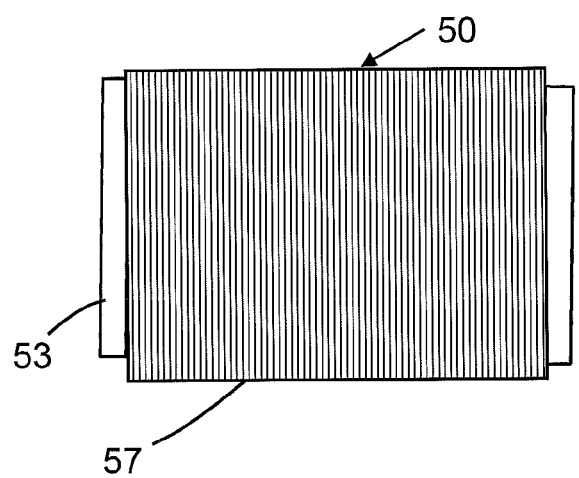
Figure 5C:
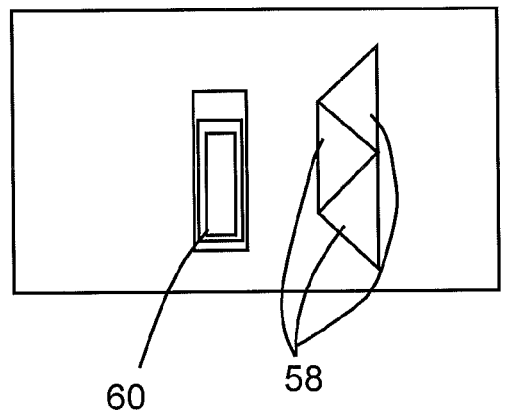

A first preferred construction of coil chamber 50 is illustrated in FIGS. 5A and 5B. Winding core 51 has winding coil 57 placed on the exterior thereof. Winding coil 57 comprises conductive material, preferably copper wire, wound about the winding core 51. The copper wire of winding coil 57 is placed on the exterior surface of winding core 51, and wound thereabout in a helical manner. Each rotation of the copper wire is known as a "turn." Each portion of copper wire placed during a turn abuts against the prior laid turn, thereby covering the entire exterior portion of the central tube 52 of winding core 51. When the end of central tube 52 opposite the end where the winding was commenced is reached in the winding process, the winding of copper wire of winding coil 57 is continued in the opposite direction along the layer of copper wire already wound onto central tube 52. The winding process continues, placing a new layer of copper wire atop the prior laid layer. The dimensions of winding core 51 is determined by the number of turns and the capacitance of capacitor bank 30 (not shown). The number of turns is calculated to maximize the amount of current passing through winding coil 57 when capacitor bank 30 is discharged. Preferably, winding coil 57 comprises about 1000 turns. The foregoing circuit configuration allows a field strength inside the coil chamber 50 of about 2.5 Tesla.

Optionally, coil chamber 50 has magnetic elements 58 placed in the interior portion thereof. Magnetic elements 58 are prepared of a ferromagnetic material and help to increase the strength of the magnetic field generated by current passing through winding coil 57. The strength of the magnetic field inside the coil chamber 50 is related to the number of turns and the current flowing through the winding coil 57 by the following:

$$B = i_o n / (r^2 + l^2)^{1/2}$$

where $i_o$ is the current in the loop, n is the number of turns in winding coil 57, r is the radius of the winding coil 57, and l is the length of winding coil 57.

Figure 8A:
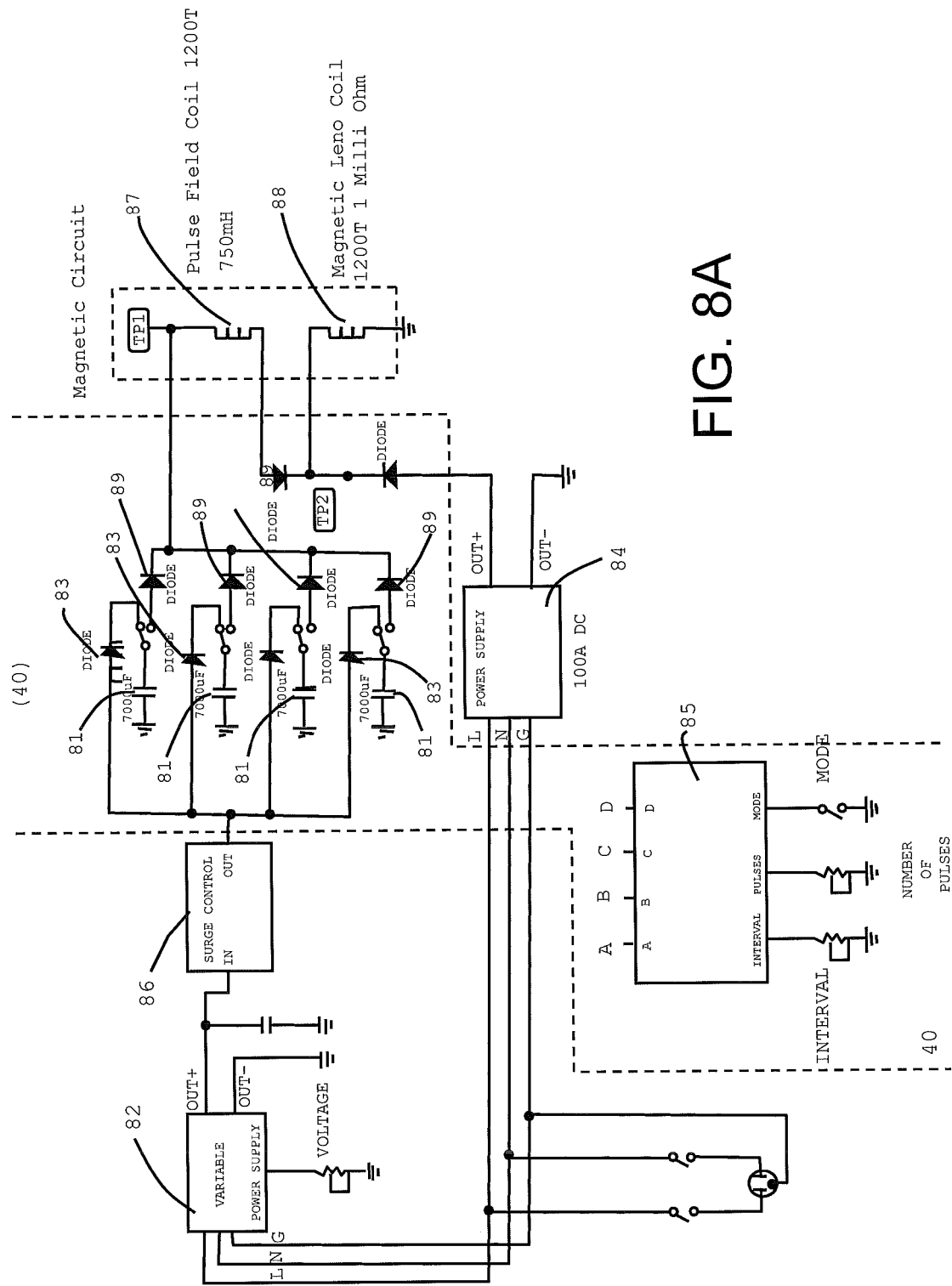
FIG. 8A is a schematic showing the wiring of the power source, capacitor bank, switching/junction box and coil chamber of a second embodiment of the device of the invention.

A second preferred embodiment for wiring the connections of the device of the current invention, including power sources 82, 84, capacitors 81, junction-switching box 80, and winding coils 87, 88 is illustrated in FIG. 8A. Junction-switching box 80 comprises a circuit of switches and diodes, as pictured in FIG. 8A. Capacitor switches A, B, C, and D selectively electrically connect capacitors 81 with variable output power source 82 and coils 87, 88. Each capacitor switch A-D has two positions. When capacitor switches A-D are placed in the up position, the variable power source 82 is connected to the capacitors 81 through surge control element 86 and diodes 83. With capacitor switches A-D in the up position the capacitors 81 are charged by the variable output power source 82. With switches A-D in the down position, the capacitors 81 are connected to coils 87, 88 through diodes 89.

Figure 8B:
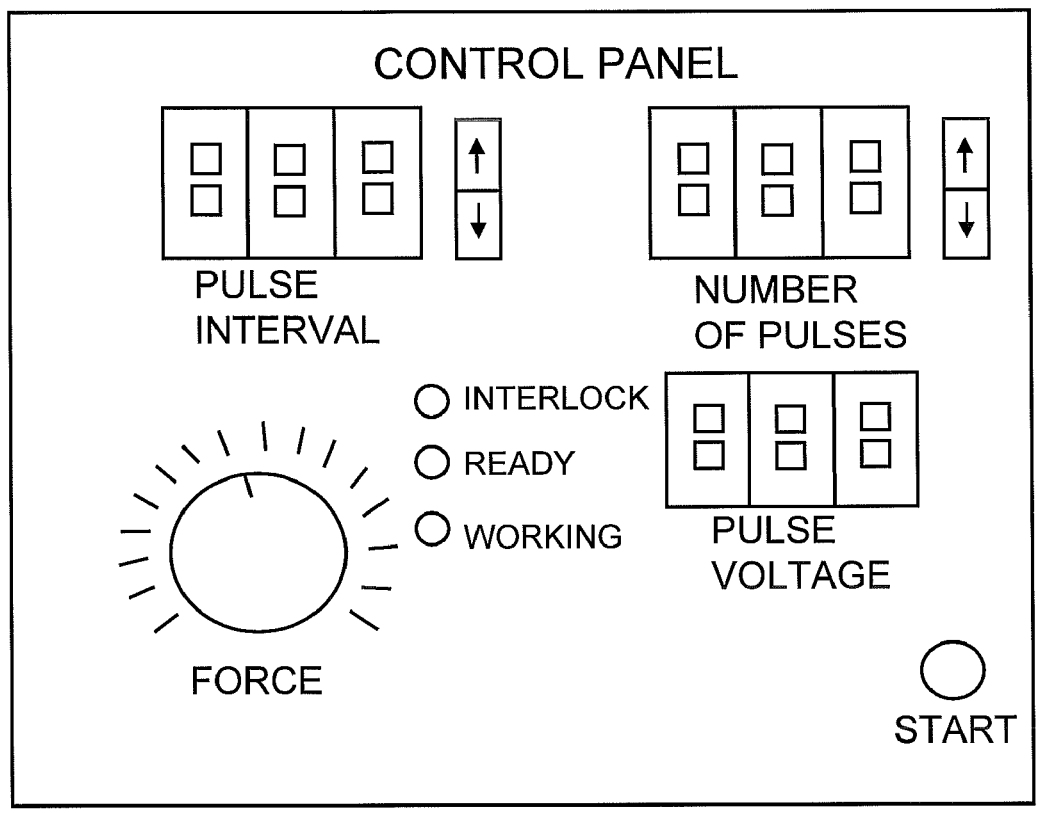
FIG. 8B is a front elevational view of the control panel of the device of the invention.
Figure 12:
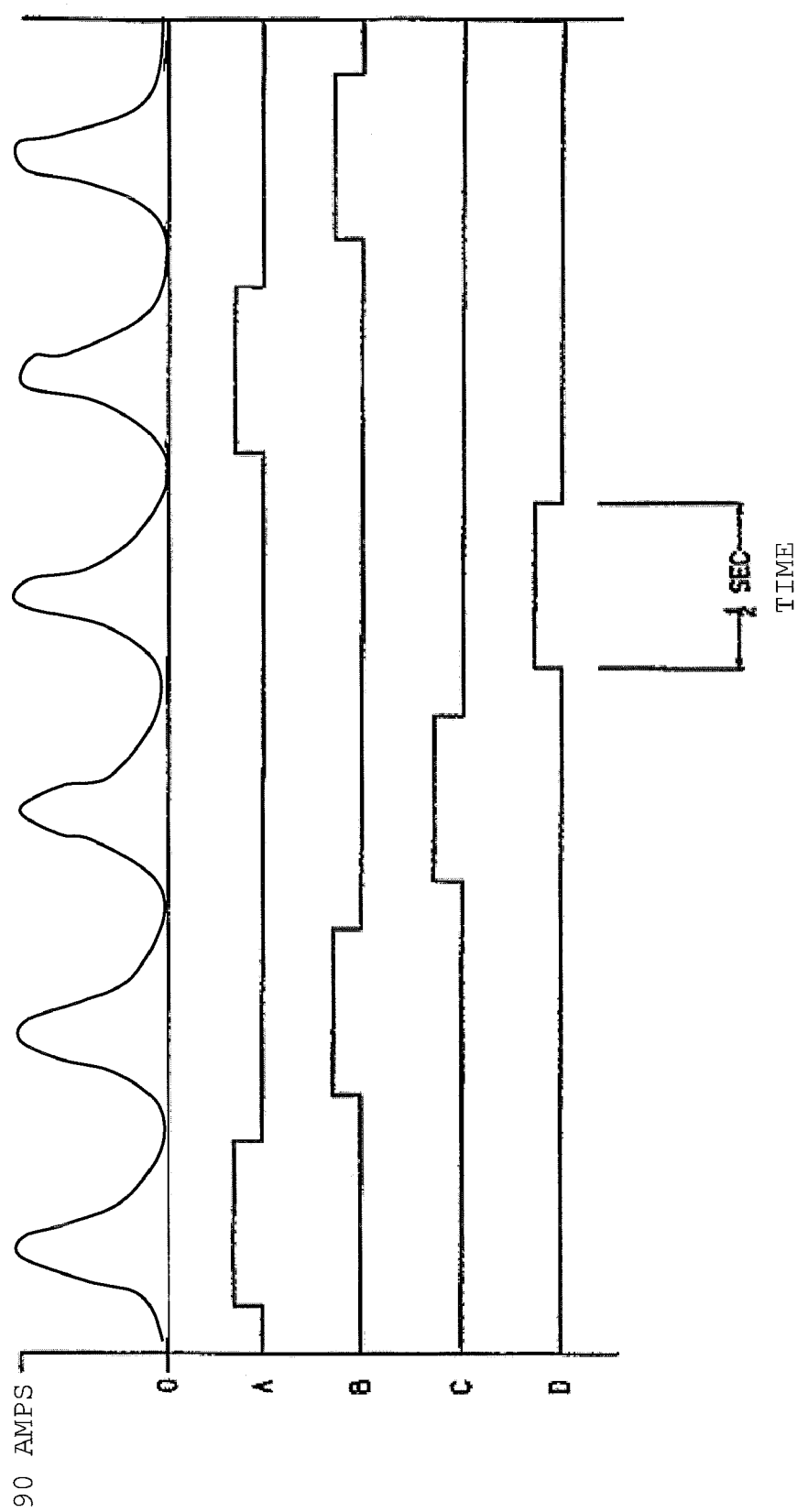
FIG. 12 is an illustration of a timing diagram for generating a series of pulses for delivery to the winding coil.
Figure 13:
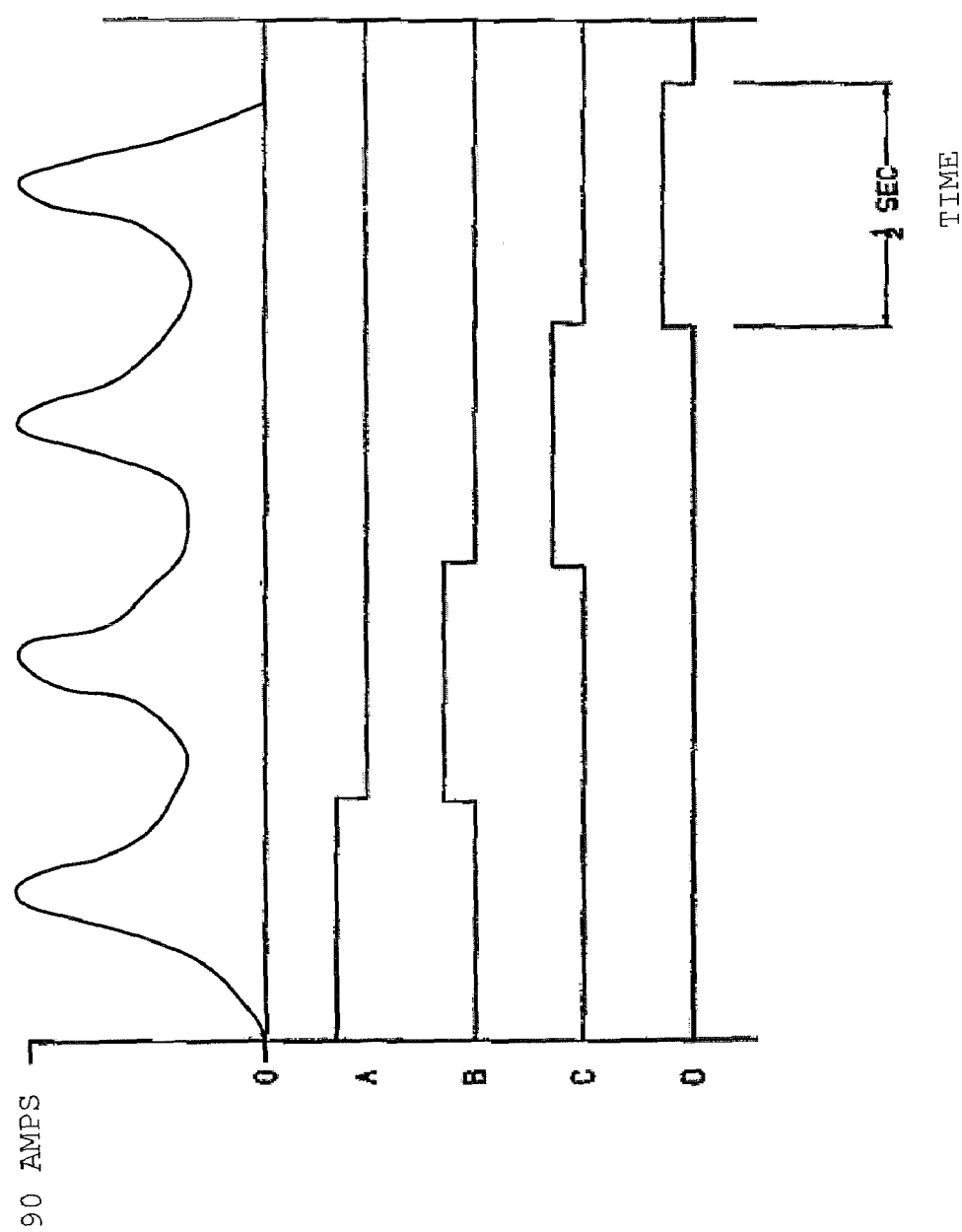
FIG. 13 is an illustration of a timing diagram for generating a series of overlapping pulses for delivery to the winding coil.

Timing switch 85 controls the timing of the switching of capacitor switches A-D. Timing switch 85 is preferably a rotating cam or more preferably an electronic timing switch. The circuit of junction-switching box 80 allows the capacitors 81 to be charged individually or as sub-groups wired in parallel (to facilitate rapid charging) and discharged sequentially to create a series of pulses in coils 87, 88 FIG. 12. The timing of timing switch 85 is preferably selected, with respect to the discharge rate of capacitors 81, to cause sequential pulses from capacitors 81 to overlap in time, FIG. 13. These pulses are delivered to primary coil 87 and secondary coil 88. These coils are constructed with the primary coil 87 containing more turns than the secondary coil 88. Preferably, the primary coil 87 contains six times more turns than the secondary coil 88. The sample chamber 96 is located within secondary coil 88, FIG. 11. Having fewer turns in the secondary coil 88, while maintaining a larger number of turns in this primary coil 87, minimizes heating of the sample contained within secondary coil 88 while maintaining a strong magnetic field. FIG. 8B illustrates a front view of the front panel associated with the circuit of FIG. 8A.

Figure 9:
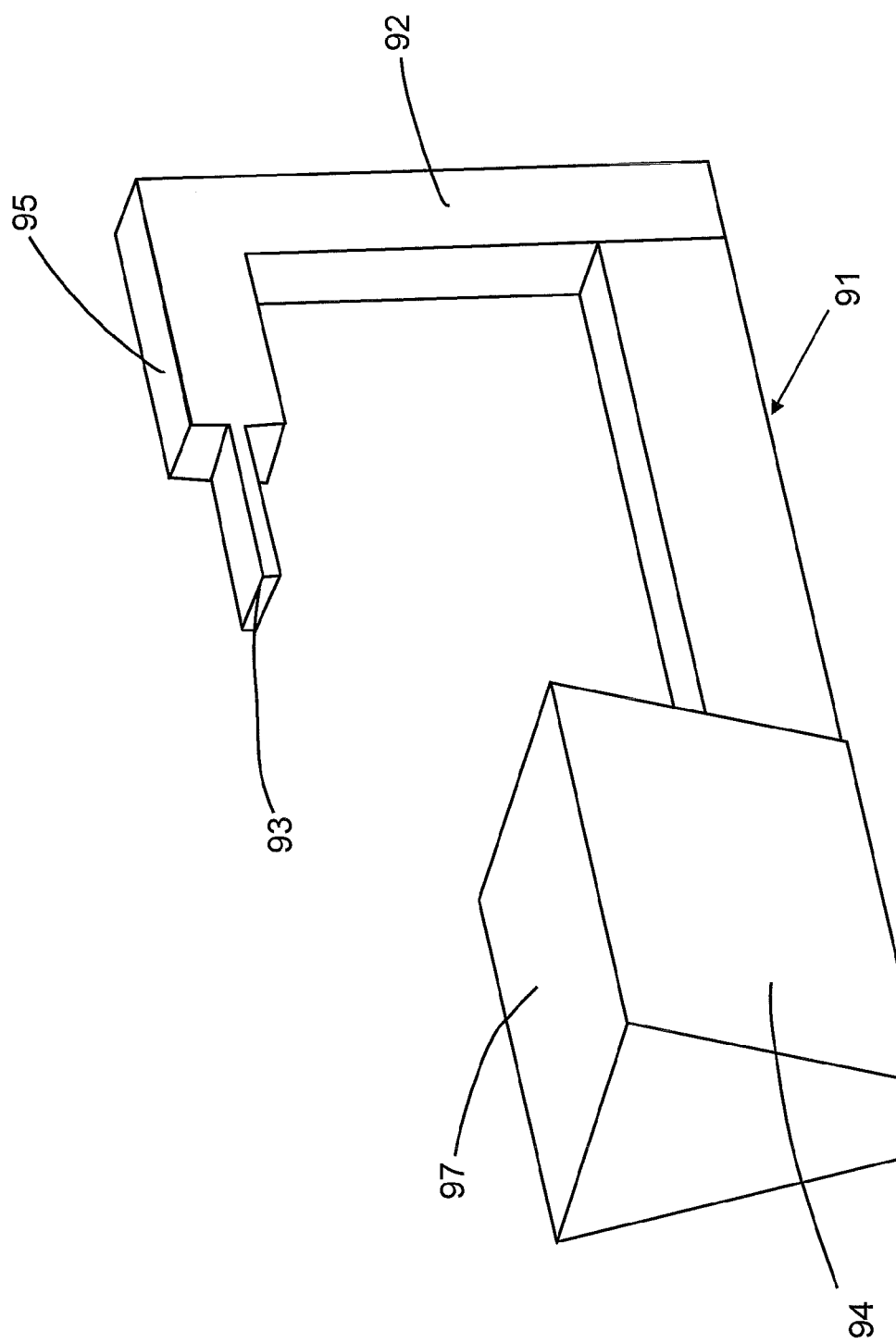
FIG. 9 is a perspective view of a second embodiment of the winding core of the device of the invention.
Figure 10:
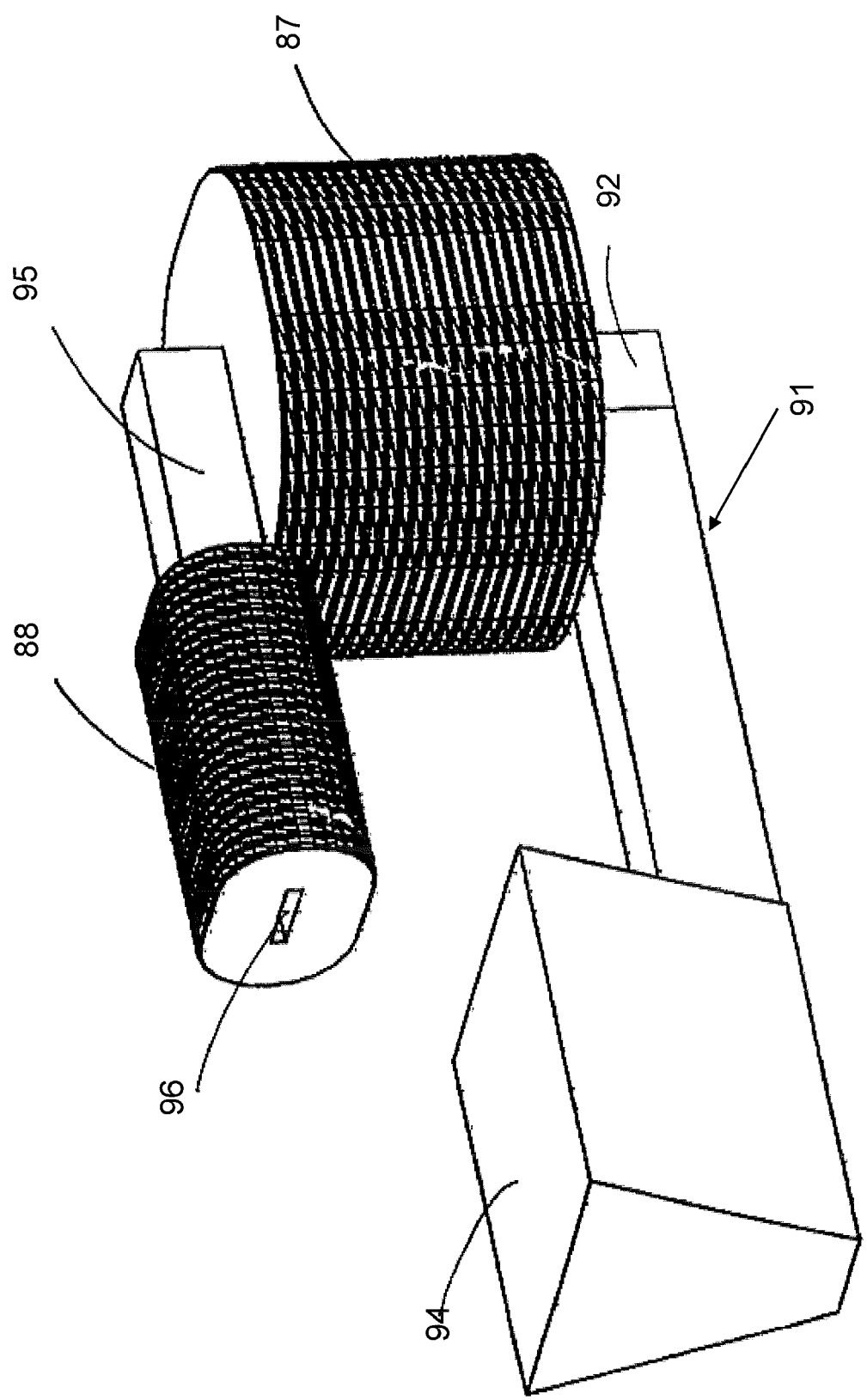
FIG. 10 is a perspective view of the winding core of FIG. 9 with the coils in place.
Figure 11:
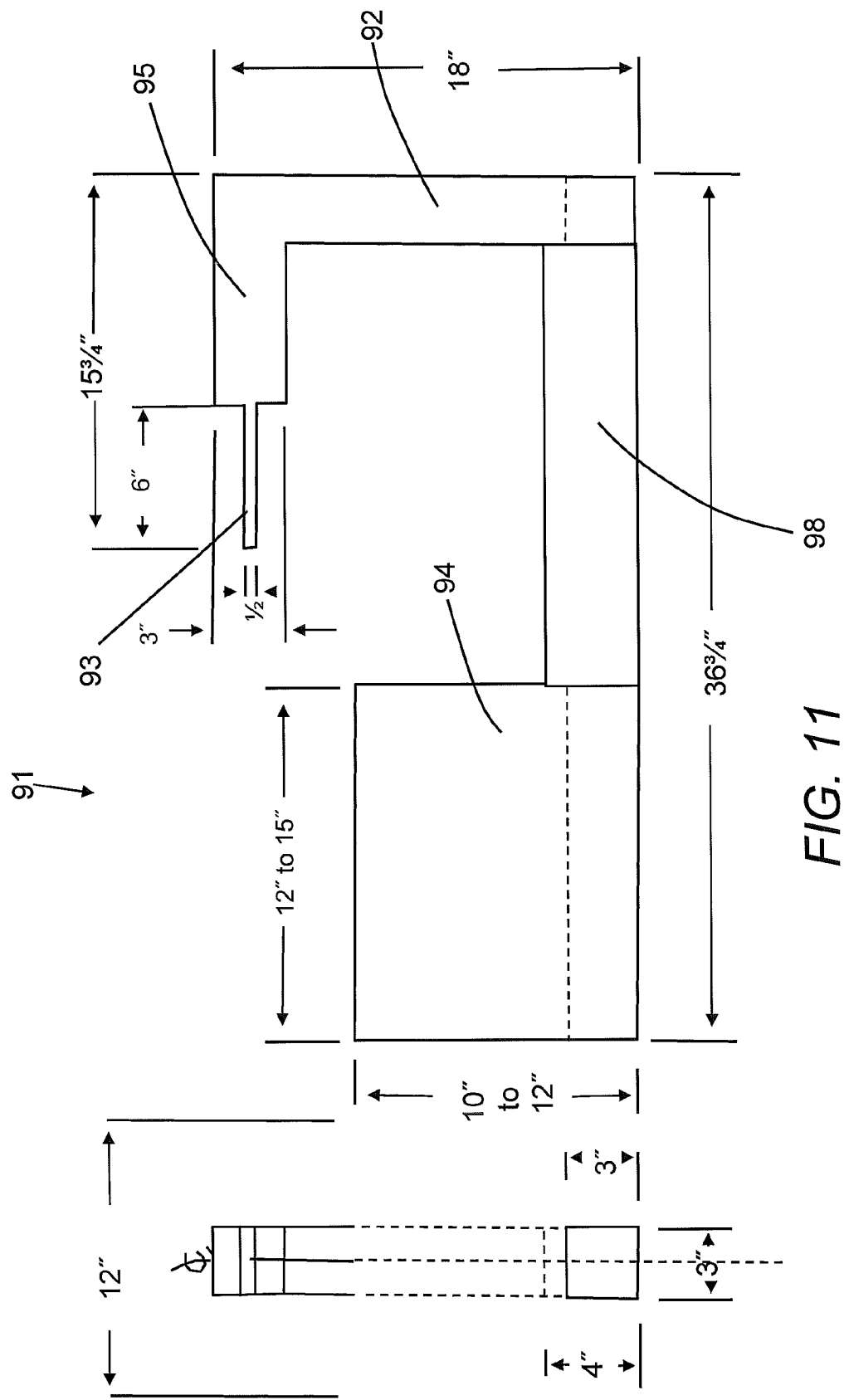
FIG. 11 is a side elevational view of a second embodiment of the winding core of the device of the invention.

FIGS. 9-11 illustrate a second preferred embodiment of a winding core 91 for use with the second preferred embodiment of the wiring the connections, discussed above. Winding core 91 comprises a vertical post 92, secondary coil core 93, horizontal post 95, horizontal bar 98 and reduced field intensity return pole 94 which are operably connected. Preferably vertical post 92, horizontal post 95, and secondary coil core 93 form a monolithic structure. Winding core 91 can be manufactured from any ferromagnetic material. Preferably, winding core 91 is made from transformer laminate. Rectangular horizontal post 95 extends at 90° from rectangular vertical post 92. The end of horizontal post 95 distal to vertical post 92, secondary coil core 93, is formed to receive secondary coil 88. Preferably, secondary coil core 93 has a decreased cross sectional area compared to that of horizontal post 95. Vertical post 92 can be of any shape that will allow placement of winding coils 87 on the exterior thereof. Secondary coil core 93 can be of any shape that permits generation of a laminar magnetic field of uniform density. Preferably secondary coil core 93 has a cross sectional shape that is rectangular. Preferably secondary coil core 93 has dimensions of about 3 inches by about 0.5 inches in cross section and length of about 6 inches, FIG. 11. Preferably vertical post 92 has dimensions of about 3 inches by about 3 inches in cross section, and horizontal post 95 has dimensions of about 3 inches in width by about 3 inches in height. Rectangular horizontal bar 98 extends at 90° from rectangular vertical post 92 and lies parallel to horizontal post 95. The end of horizontal bar 98 distal to vertical post 92 is operably connected to reduced field intensity return pole 94.

Return pole upper face 97 is designed to minimize the strength of the magnetic field in the vicinity of reduced field intensity return pole 94 while maximizing magnetic field strength in chamber 96. The surface area of return pole upper face 97 relative to that of secondary coil core 93 and its position relative to secondary coil core 93 are designed to achieve this effect. Preferably, the surface area of return pole upper face 97 is 100 times the surface area of secondary coil core 93. Preferably, return pole upper face 97 lies below a horizontal plane containing secondary coil core 93 and lies more distal to primary coil 87 than the distal-most extremity of secondary coil 88. The shape of reduced field intensity return pole 94 may be any shape that maintains the above mentioned relationships between the relative areas and locations of return pole upper face 97 and secondary coil core 93. Preferably the shape of reduced field intensity return pole 94 is chosen to additionally reduce its weight. A preferred shape is trapezoidal in cross-section, having a reduced area at the surface opposite to return pole upper face 97 as seen in FIG. 9.

Primary coil 87 and secondary coil 88 are wrapped around vertical post 92 and lens coil core 93, respectively. Winding coils 87, 88 comprise conductive material, preferably copper wire. The copper wire of winding coils 87, 88 is placed on the exterior surface of winding core 91, and wound thereabout in a helical manner. More preferably, the winding coils 87, 88 comprise flat conductive bands whose flat shape permit decreased weight of the winding coils 87, 88. The winding begins with primary coil 87. Each portion of copper wire placed during a turn abuts against the prior laid turn, thereby covering the entire exterior portion of the vertical post 92 of winding core 91. When the end of vertical post 92 opposite the end where the winding was commenced is reached in the winding process, the winding of copper wire of winding coils 87 is continued in the opposite direction along the layer of copper wire already wound onto vertical post 92. The winding process continues, placing a new layer of copper wire atop the prior laid layer. The dimensions of vertical post 92 is determined by the number of turns and the capacitance of capacitors 81. Preferably coil 87 is composed of several modular coils operably connected and stacked on top of one another around vertical post 92. Preferably, 8 modular coils are used. The winding of secondary coil 88 proceeds in a continuous manner after winding of the primary coil 87 by running the copper wire (not shown) from the last turn of primary coil 87 along horizontal post 95, where the winding of secondary coil 88 begins. Secondary coil 88 is wound in an analogous manner to that of primary coil 87 with secondary coil 88 having fewer turns than primary coil 87. The number of turns is calculated to maximize the amount of current passing through coils 87, 88 when capacitors 81 are discharged. Preferably, primary coil 87 comprises about 1200 turns and secondary coil 88 comprises about 200 turns. The winding of secondary coil 88 further differs from that of primary core 87 in that the winding extends beyond the end of secondary coil core 93 to from sample chamber 96 where the support base (not shown) is placed. This allows a field strength inside the coil chamber 50 of about 3 Tesla. and 0.3 Tesla at the return pole upper face 97. Such a reduced field at the return pole upper face 97 has the benefit of protecting an operator from the stronger magnetic field when the return pole upper face 97 is positioned between the operator and chamber 96.

Optionally, chamber 96 has magnetic elements (not shown) placed in the interior portion thereof. Magnetic elements are prepared of a ferromagnetic material and help to increase the strength of the magnetic field generated by current passing through winding coils 87, 88.

Figure 7A:
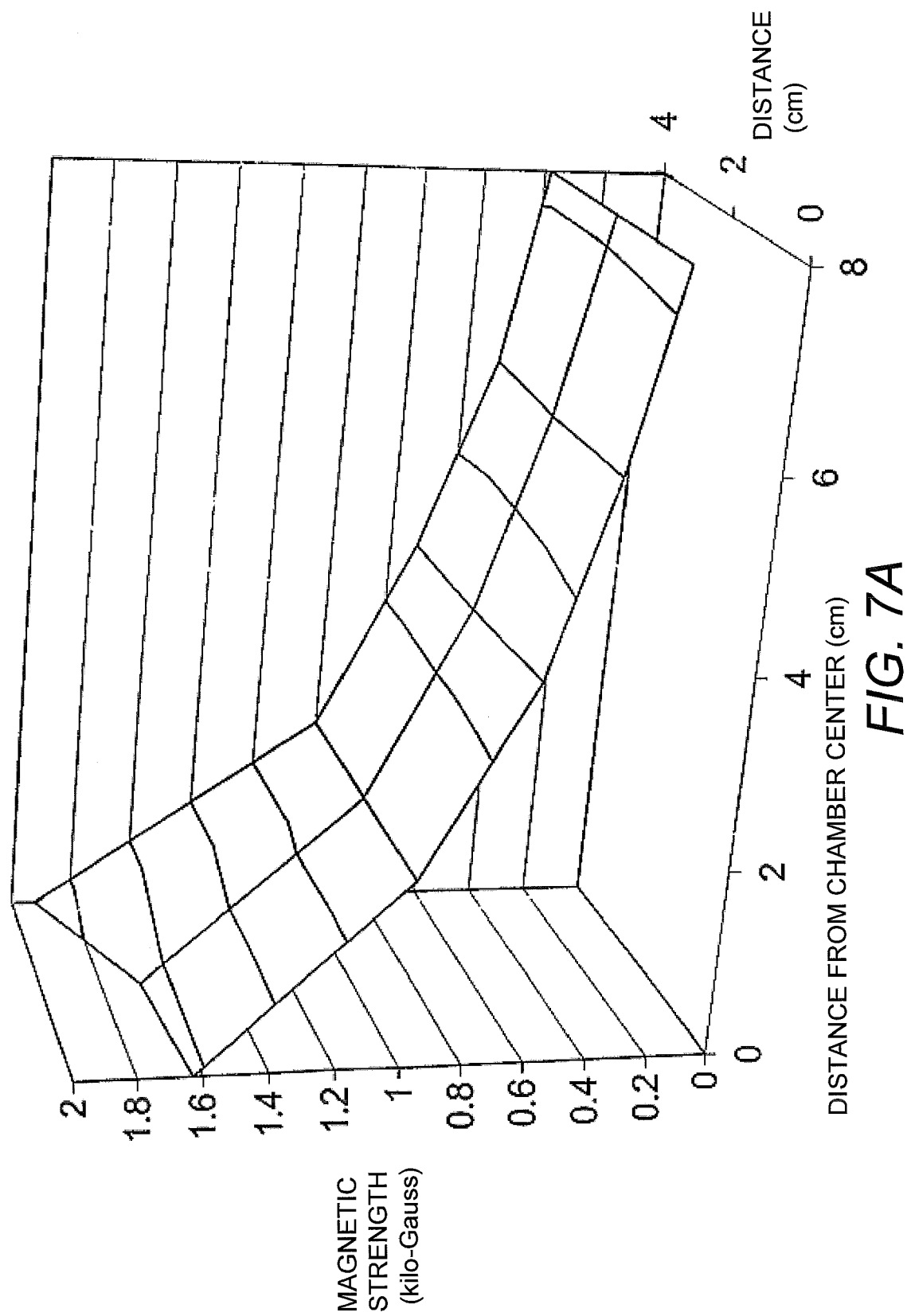
FIG. 7A is a graph showing the lines of force in kilo-gausses across a horizontal plane in the empty cell separation chamber using continuous DC current. The left most values are measurements at the center of the chamber's field. The successive values show measurements every 2 centimeters away from the center along a central horizontal plane.
Figure 7B:
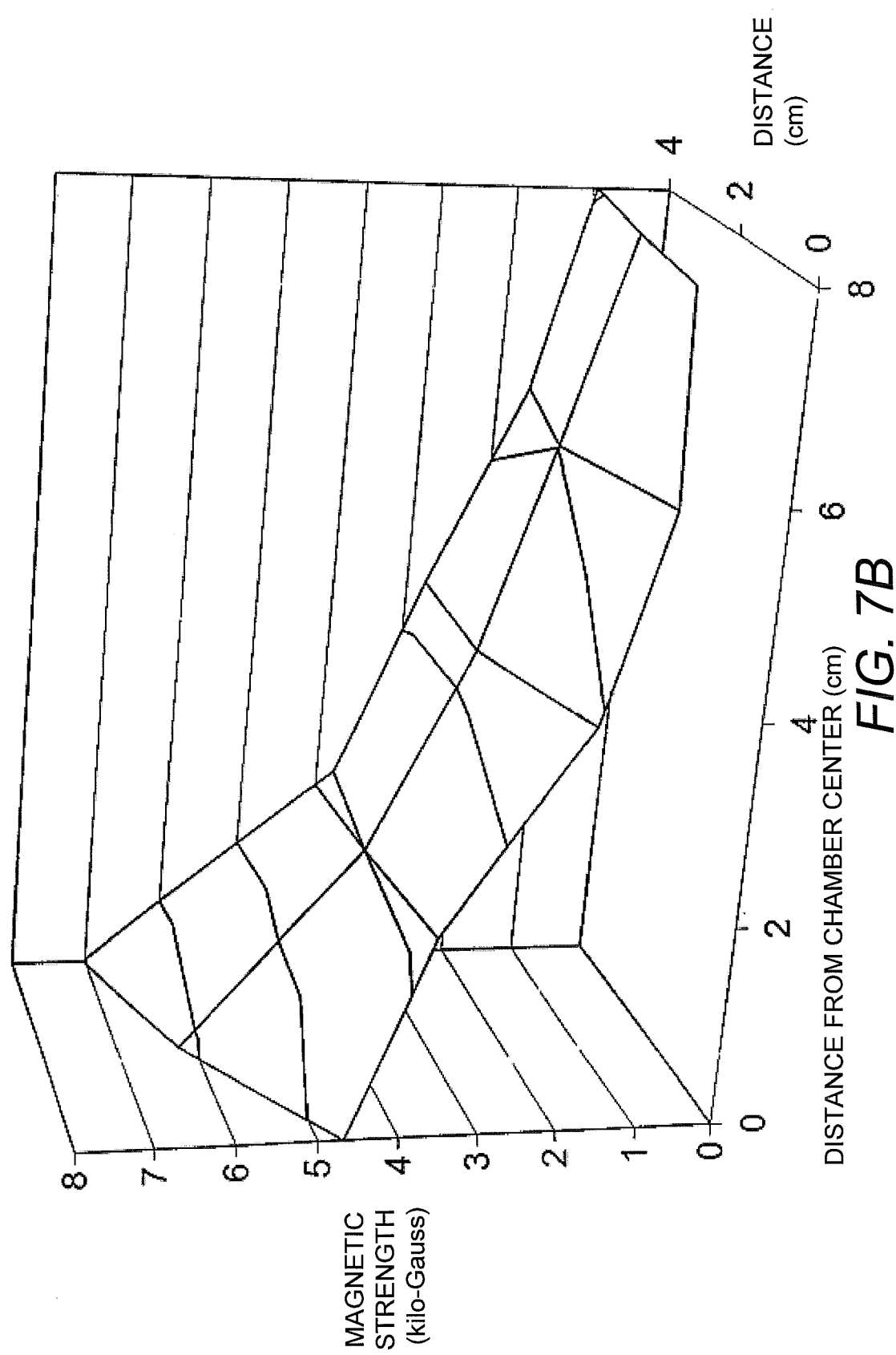
FIG. 7B is a graph showing the lines of the force in kilo-gausses at the same sites as seen in FIG. 7A and indicating the increase generated by a one second pulse through the core following the discharge of the capacitors in series. Note that this pulse results in a greater than three fold increase in magnetic force at any given site in the chamber.

The effect of pulsing the circuit of the first preferred embodiment on the resulting magnetic field is illustrated in FIGS. 7A and 7B. FIG. 7A shows the lines of force in kilo-gausses across a horizontal plane in the empty coil chamber 50 using continuous DC current. The values plotted are shown in Table 1. The numbers in the column to the left are measurements at the center of the chamber's field. The successive columns show measurements every 2 centimeters away from the center along a central horizontal plane.

FIG. 7B shows the lines of the force in kilo-gausses at the same sites as seen in FIG. 7A and indicates the increase generated by a one second pulse through the core following the discharge of the capacitors in series. The values plotted are shown in Table 2. This pulse results in a greater than three fold increase in magnetic force at any given site in the coil chamber 50.

TABLE 1

| | X | | | | |
|---|---|---|---|---|---|
| Y | 0 | 2 | 4 | 6 | 8 |
| 0 | 1.92 | 1.00 | 0.71 | 0.49 | 0.38 |
| 2 | 1.67 | 1.00 | 0.70 | 0.51 | 0.38 |
| 4 | 1.63 | 1.00 | 0.67 | 0.50 | 0.37 |

TABLE 2

| | X | | | | |
|---|---|---|---|---|---|
| Y | 0 | 2 | 4 | 6 | 8 |
| 0 | 7.03 | 3.77 | 2.74 | 1.57 | 0.95 |
| 2 | 6.20 | 4.00 | 2.78 | 1.99 | 1.28 |
| 4 | 4.69 | 3.74 | 2.05 | 1.39 | 1.50 |

Figures 6A, 6B:
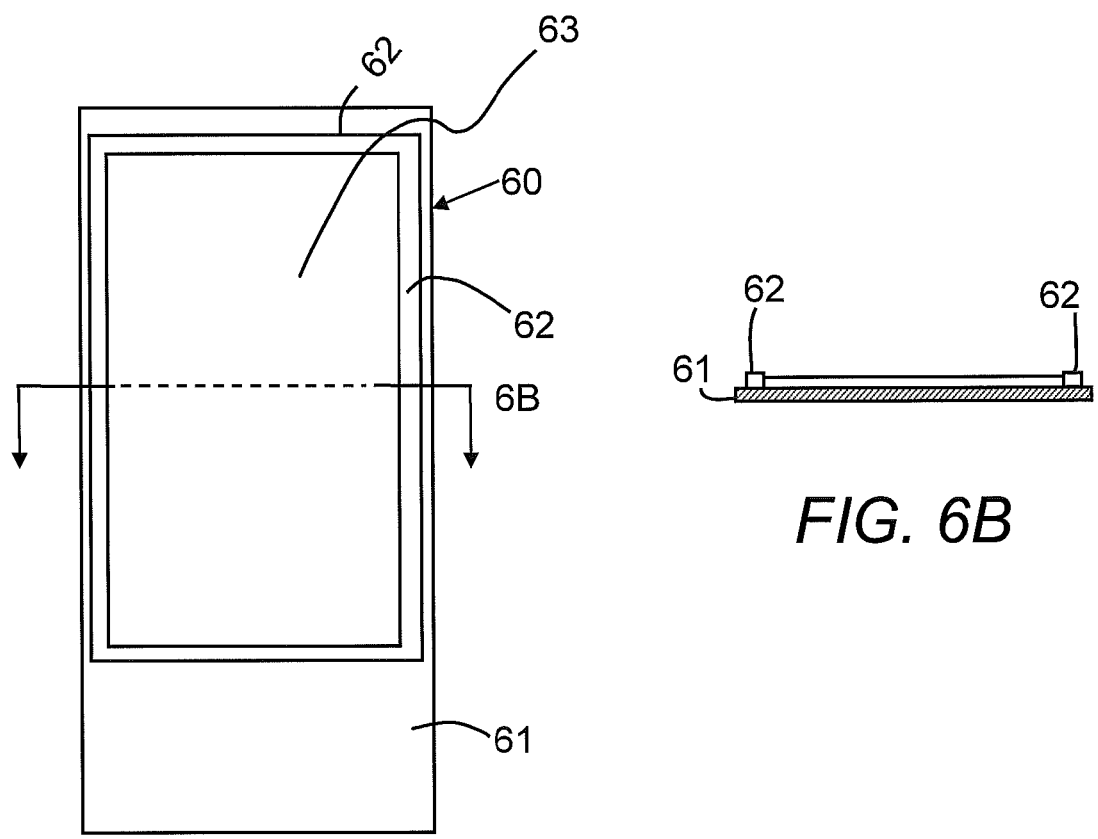
FIG. 6A is a top view of the holder for the substrate base of the invention.
FIG. 6B is a sectional view of the substrate base holder taken along line 6B in FIG. 6A.

Support base 60 is illustrated in FIGS. 6A and 6B. Support base 60 comprises a slide base 61, preferably prepared from a standard microscope slide. Slide base 60 has walls 62 placed on the upper surface thereof in a pattern creating transport area 63. Walls 62 preferably comprise glass bars. Transport area 63 is coated with a separation medium, also referred to herein as a "substrate material". The separation medium is a substance which allows differential migration of components in the solution under the effect of the magnetic field generated by current passing through winding coil 57. Separation media can be any such substance as known in the art for magnetophoretic substrates. In a preferred embodiment, the separation medium is a solution comprising a polymeric material or any other material the viscosity of which can be manipulated (e.g., high concentrations of short carbohydrates). The viscosity of the solution can be varied depending on the size and shape of the components to be magnetically separated, as would be apparent to one of skill in the art of magnetophoretic or electrophoretic separation. In general, the viscosity is adjusted such that the component to be separated is substantially unable to diffuse through the material unless the requisite magnetic field is applied. In a preferred embodiment, wherein eucaryotic cells are separated, the substrate material comprises a colloidal solution of a polymer, which is of sufficient viscosity to prevent spontaneous diffusion of the cells. A particularly preferred substrate material is methylcellulose, as described in greater detail in the sections below. Methylcellulose is advantageous because the viscosity of methylcellulose solutions can be adjusted, but also because it can be combined with various cellular growth media. (In preferred embodiments of the invention, it is desirable to grow one or more of the components separated using the methods described herein.) Moreover, methyl cellulose does not autofluoresce like other polymeric solutions (e.g., agar), thereby enabling its advantageous use with fluoresence detection methods. Other substrate materials that could be used to separate various cells or subcellular components include, but are not limited to, agarose, agar and polyacrylamide.

In preforming the method of the invention. A sample containing a component of interest (sometimes referred to herein as a "target substance") is exposed to a solution containing magnetic particles. The magnetic particles have ligands capable of directly or indirectly binding to the target substance. During contact the magnetic particles then bind with the target substance to form a complex, referred to herein as a "magnetic transport complex."

A sample of the solution containing the magnetic transport complex is placed along one edge of the transport area 63 on the support base 60, in the separation medium. The support base 60 is placed inside the coil chamber 50. The power source 20 is activated and the capacitor bank 30 is charged.

Capacitors 31 in capacitor bank 30 are charged in a parallel wired configuration. This allows the maximum charge to be placed on the capacitors in a minimum amount of time. The capacitors 31 of capacitor bank 30 are then discharged in series, releasing current into winding coil 57. This maximizes the charge released into winding coil 57.

The capacitors 31 are discharged in series in a pulsed manner. The discharge pulses last about 0.86 seconds per discharge and repeats about once every two minutes. Each pulse generates a magnetic field of at least about 0.7 Tesla, more preferably about 1.0 Tesla and further more preferably of about 2.0 Tesla.

These pulsed magnetic fields cause the component bound to the magnetic beads to move across the separation medium at a different rate than the undesired component. Eventually, the substances that have the magnetic beads bound thereto migrate away from the remaining components in the solution, and these components are removed. Additionally, the magnetic beads may be removed.

For example, a sample of blood taken from a pregnant woman was co-incubated with both a fluorescein labeled monoclonal antibody to CD 71 and with 0.1 micro meter diameter magnetic beads having a monoclonal antibody to the same antigen. The sample was placed at a starting point in the transport area 63. After a 20 min exposure in the pulsed magnetic field of the invention, phase contrast microscopy revealed the separation of cells. Virtually every cell that moved through the magnetic field was seen to be positive for CD71, as seen at 190X using a Zeiss photomicroscope with epi-fluorescence illumination and appropriate FITC filters for detection of fluorescein. The majority of cells remained at the starting line, because they did not have magnetic beads and could not cross the viscous media by diffusion. Microscopy also revealed that not all the cells moved at the same rate through the media. Under the conditions of this run, the cells were seen to move as mostly individual cells. The rare CD 71+ cells remained viable and could easily be aspirated from the separating media for further analysis.

The pulsed magnetic separation device and system described herein can be used to improve many separation applications in which magnetic separation is currently utilized. Such applications include separation of biological or non-biological substances. Referring to biological substances that can be separated, these include eucaryotic and procaryotic cells, subcellular organelles, viruses, proteins, nucleic acids, carbohydrates, ligands or complex molecules comprising nucleic acids, proteins, lipids and/or carbohydrates. Referring to non-biological applications, these include removal of toxic compounds from industrial waste streams or other environmentally hazardous sites, or the detection of contaminants in sewage treatment processes and the like.

A material is separable by the methods described herein if the material possesses at least one characteristic determinant, which is capable of being recognized by and bound to a ligand which is attachable to a magnetic particle. Materials having such characteristic determinants are referred to herein as "target substances" or "desired components". If the target substance is a cell, it is referred to herein as a "target cell." The term "characteristic determinant" is used herein to refer to substances such as antigens, haptens, and other complex molecules (e.g., carbohydrates, glycoproteins, etc.), which are capable of the above-described specific binding to a ligand. "Ligand" is used herein to refer to any substances or group of substances having a specific binding affinity for a given characteristic determinant, to the substantial exclusion of other substances. Monoclonal antibodies are preferred for use as the ligand. However, polyclonal antibodies or non-antibody receptors, including antigens for antibody-producing cells or antigen processing cells, lectins, such as concanavalin A and various agglutinins, biotin-labelled reagents or hapten-labelled reagents, may be used, if desired.

The methods of the invention may be structured as "direct" or "indirect" protocols, or some combination thereof. In the direct protocol, the ligand is attached directly to the magnetic particles, and magnetic complexes are obtained by incubating test samples containing the target substance with the ligand-coated particles. In the indirect protocol, the target substance is incubated with a free ligand and the magnetic particles comprise a capture agent capable of recognizing and binding specifically to the ligand, so as to form a complex comprising target substance, ligand, capture agent and magnetic particle.

For the indirect protocol, suitable capture agents include Protein A or Protein G, where immunoglobulin is used as the ligand; avidin, where a biotin-labelled reagent is used as the ligand; and anti-hapten, where a hapten-labelled reagent is used as the ligand. Either biotin or a hapten may be used to facilitate capture of lectin ligands, e.g., concanavalin A and various agglutinins, which bind selectively to membrane-containing target substances whose characteristic determinants comprise carbohydrate or glycoprotein components. Hapten/anti-hapten pairs suitable for this purpose include dinitrophenol (DNP)/anti-DNP, fluorescein/anti-fluorescein or arsanilic acid/anti-arsanilic acid.

The magnetic separation methods and devices of the invention may be used to carry out cell separation for isolation and/or analysis of specific cell populations. Because high levels of recovery and purity are achievable by the methods of the invention, these methods are particularly suitable for removal or isolation of rare cells from a mixed population of cells. Such separations include, but are not limited to, enrichment of stem cells from bone marrow or peripheral blood, isolation of fetal cells from maternal blood, isolation of transfected cells, and removal or isolation of tumor cells from various mixed cell populations. Such separations may be accomplished by positive selection or negative depletion, or both, in accordance with the present invention. (It will be appreciated that, according to the definition of "target cell" set forth above, a cell subset enriched by negative depletion is actually a non-target cell, since it is not bound to an antibody or other ligand. Instead, cells to be depleted from the population are target cells, within the definition.) Cells recovered by such separation methods may be utilized for numerous purposes, including further analysis (e.g., by flow cytometry or other methods) or for therapeutic purposes (e.g., re-introduction of enriched populations of stem cells to patients).

The methods and devices of the present invention may be used to particular advantage in a combined strategy for isolating a small population of rare cells (e.g., stem cells, fetal cells) from a mixed cell population, while simultaneously purging the population of unwanted cells (e.g., tumor cells). This may be accomplished simply by incorporating a receptor for the unwanted cell type in the negative depletion separation systems described hereinabove. It will be appreciated that, in cases wherein the unwanted population comprises a subpopulation of cells already targeted for depletion in such a system, no additional antibodies need be added. One example of this situation is in various leukemias, wherein the unwanted target cell populations are B-cells, already targeted for removal in the hematopoietic stem cell enrichment process. In other embodiments, additional monoclonal antibodies directed to various tumor cells or other unwanted cells are added to the negative depletion antibody mix.

Although the use of the methods and devices of the invention are exemplified herein by the separation of rare cell populations, as described above, it will be apparent to those of skill in the art that the methods may also be used for other separations according to the same general procedures. These include, but are not limited to, the separation of various bacteria and parasites from fecal matter, urine, sludges, slurries and water (e.g., ground water or streams); or in the separation of various bacteria, fungi or other target substances from food products or other sources.

EXPERIMENTS

The method and apparatus of the current invention has been used to isolate CD71+ cells from the rest of the whole blood population. These experiments yielded CD 71+ cell populations that are close to 100% pure, using 8 ml peripheral blood sample. To our knowledge, no other device currently available has the sensitivity to address this possibility.

Blood Collection and CD 71+ Cell Selection

Eight milliliters of peripheral whole blood was collected in a sodium heparin tube and is then diluted 1:2 with Puck's Balanced Salt Solution (PBS). This diluted blood was gently layered onto a triple HISTOPAQUE discontinuous density gradient (3 ml, 1119; 2 ml, 1083; 1 ml, 1077—Sigma Co.). After spinning the gradient at 1400-1500 rpm for 20 minutes, the lymphocyte and granulocyte layers were collected and stored over ice. Panning methods to remove CD 45+ cells from the granulocyte layer was done by first coating a petri-dish with 11 ml of goat anti-mouse IgG (10 μg/ml in 0.05 M Tris Buffer-Capel-INC Pharm. Inc.) at room temperature. The petri-dish was washed three times with PBS and once with 1% fetal calf serum in PBS. To 2-3 million cells/ml of the granulocyte layer, was added 10 μl of CD45 monoclonal antibody (10 μg/ml in PBS—Immunotech, Inc.) at room temperature for 20 minutes. One ml of this cell suspension was put onto the IgG treated dish and placed in the refrigerator at 4 degrees centigrade for 2 hours. After binding the CD 45+ cells to the petri dish, the non-adherent cells containing the CD 71+ population were collected into a five milliliter glass conical tip centrifuge tube. To this cell suspension an equal volume of water was added and this solution sat at room temperature for ten minutes to lysis any red blood cells. The cells were then centrifuged at 900 rpm for 10 minutes, the supernatant was removed and the cell button was reconstituted in about one milliliter of 1×PBS buffer. These cells were then processed for either micro bead or fluorescent dye attachment.

Micro Bead and Fluorescent Dye Attachment

Two types of CD 71 monoclonal antibody-coated magnetic beads were used, which differ in their size. The larger beads were super-magnetic, mono dispersed polystyrene micro-spheres averaging 4.5 microns in diameter (Dynal. Inc. N.Y. Cat #M-450). The smaller superparamagnetic micro beads were extremely small with a diameter range of between 50 and 100 nanometers (Miltenyi Bioec Co. Ca. Cat# 426-01). Paramagnetic, as used herein, refers to a material which is magnetizable when placed within a magnetic field. Attachment was accomplished by taking 20 μl of the bead solution, adding it to 1 ml of cell suspension and incubating at a temperature of between 0° and 4° C. for 1 hour.

The desired cells were labeled with fluorescent compounds to locate them in the methylcellulose media after magnetic separation, while maintaining their viability for tissue culturing. Direct immuno-fluorescence staining of the cells possessing the CD 71 surface antigen by monoclonal antibody conjugated with fluorescein (FITC, Becton-Dickson Co. Cat #347513) was done by adding 20 μl of FITC-labeled-CD 71 to about 1 ml of cell suspension and incubating at a temperature of between 0° and 4° C. for 30 minutes. In experiments that co-labeled the cells with CD 71 micro-beads and FITC antibody, the beads were added first for a 1 hour incubation followed by the FITC antibodies for a 30 minute incubation.

Separation Media Preparation

Methylcellulose solutions of various viscosities were used. Aqueous solutions were prepared using methylcellulose powder (Sigma Chemical Co. Mo. Cat #9000467-5), 400 centipoises in distilled deionized water. This solution was stirred overnight to completely suspend the methylcellulose and used fresh for each experiment (viscosity data on the different percent methylcellulose solutions is given in Table 3).

TABLE 3

| | Concentration = 1.0% dyn/cm$^2$ | | | Concentration = 1.5% dyn/cm$^2$ | | | Concentration = 2.0% dyn/cm$^2$ | | |
|---|---|---|---|---|---|---|---|---|---|
| rads/s W | G | G" | ETA* | G | G" | ETA | G | G" | ETA |
| 0.79 | 0.06 | 0.36 | 0.46 | 0.12 | 1.42 | 1.79 | 0.69 | 5.00 | 6.35 |
| 1.00 | 0.05 | 0.44 | 0.44 | 0.17 | 1.77 | 1.78 | 0.88 | 6.18 | 6.24 |
| 1.26 | 0.05 | 0.55 | 0.44 | 0.19 | 2.19 | 1.75 | 1.12 | 7.65 | 6.14 |
| 1.59 | 0.08 | 0.66 | 0.42 | 0.23 | 2.74 | 1.74 | 1.41 | 9.49 | 6.05 |
| 2.00 | 0.08 | 0.83 | 0.42 | 0.28 | 3.38 | 1.70 | 1.79 | 11.65 | 5.91 |
| 2.51 | 0.19 | 1.05 | 0.43 | 0.24 | 4.18 | 1.67 | 2.32 | 14.15 | 5.71 |
| 3.16 | 0.26 | 1.52 | 0.49 | 0.47 | 5.31 | 1.69 | 2.76 | 17.85 | 5.71 |
| 3.98 | 0.04 | 1.67 | 0.42 | 0.59 | 6.75 | 1.70 | 3.75 | 21.57 | 5.50 |
| 5.01 | 0.00 | 1.97 | 0.39 | 0.49 | 8.24 | 1.65 | 4.69 | 26.79 | 5.43 |
| 6.31 | 0.19 | 2.42 | 0.39 | 0.82 | 10.08 | 1.60 | 6.05 | 32.64 | 5.26 |

TABLE 3-continued

| | Concentration = 1.0% dyn/cm² | | | Concentration = 1.5% dyn/cm² | | | Concentration = 2.0% dyn/cm² | | |
|---|---|---|---|---|---|---|---|---|---|
| rads/s W | G' | G" | ETA* | G' | G" | ETA | G' | G" | ETA |
| 7.94 | 0.36 | 3.13 | 0.40 | 1.11 | 12.63 | 1.60 | 7.84 | 39.88 | 5.12 |
| 10.00 | 0.16 | 4.05 | 0.41 | 1.64 | 16.12 | 1.62 | 9.90 | 48.20 | 4.92 |
| 12.59 | 0.46 | 5.17 | 0.41 | 2.36 | 19.71 | 1.58 | 12.99 | 59.12 | 4.81 |
| 15.85 | 0.35 | 6.11 | 0.39 | 3.04 | 24.16 | 1.54 | 16.55 | 72.24 | 4.68 |
| 19.95 | 0.36 | 7.73 | 0.39 | 4.50 | 30.19 | 1.53 | 21.00 | 87.78 | 4.52 |
| 25.11 | 1.04 | 9.92 | 0.40 | 5.89 | 37.16 | 1.50 | 27.23 | 106.80 | 4.39 |
| 31.62 | 1.57 | 12.17 | 0.39 | 8.30 | 45.65 | 1.47 | 34.87 | 129.80 | 4.25 |
| 39.80 | 2.22 | 15.49 | 0.39 | 11.33 | 56.20 | 1.44 | 44.93 | 157.60 | 4.12 |
| 50.10 | 3.85 | 19.27 | 0.39 | 15.38 | 69.14 | 1.41 | 57.89 | 191.10 | 3.99 |
| 63.08 | 5.89 | 23.91 | 0.39 | 20.93 | 84.94 | 1.39 | 74.94 | 231.40 | 3.86 |
| 79.41 | 9.38 | 29.42 | 0.39 | 28.71 | 104.90 | 1.37 | 97.88 | 281.30 | 3.75 |
| 99.97 | 14.57 | 35.89 | 0.39 | 40.27 | 130.10 | 1.36 | 129.60 | 343.20 | 3.67 |

A comparison of the G' (less modular-fluid nature), G" (storage modular-solid nature) and ETA* (complex viscosity) of the 1.0%, 1.5%, 2.0% methylcellulose solution (400 centipoises) used as cell separation media Note that in all these solutions, the G" level exceeds the G' level at all rotation frequencies, indicating the colloidal nature of these solutions. Note the increase in solid like nature of the solutions and the complex viscosity as the solution concentration increases. The fluid properties impact the magnetically induced transport behavior through the solution and were designed such that the cells do not migrate by diffusion.

Magnetic Separation

A glass slide was made with methyl cellulose transport medium having the desired viscosity layered onto its surface. An aliquot of the solution containing the magnetic bead-labeled cells was placed at one edge of the methylcellulose to form a starting line. When the magnetic field was activated, the cells were drawn towards the center of the chamber in a linear manner. This produced a line of cell movement away from the starting point, creating a separation from the undesired component. The separated cells can be seen to create a band, that can be taken off the slide using a stereoscope to locate the separated cells, and a pipette to aspirate off these cells.

Cell Aspiration of CD 71+ Cells by Micro-Manipulation

Once the cells with magnetic beads have been separated from the non-magnetic cells, they form a line that can be seen under a stereo microscope. The tip of a pipette that is on a micro manipulator can be placed at this cell line and the cells can be aspirated into the pipette using negative pressure. The cells that have been withdrawn can then be placed onto a microscope slide for multicolor FISH and fluorescent antibody staining techniques to analyze for chromosome abnormalities. Individual cells can also be placed into wells for PCR studies.

Fluorescent In-Situ Hybridization (FISH) Analysis of CD 71+ Isolated Cells

Slides having cells for FISH are fixed in a 3:1 methanol to acetic acid solution several times and are treated for in situ hybridization using standard techniques for multicolor FISH analysis (Zhu et. al, 1994). These methods include denaturing of the probe and target DNA, overnight hybridization, and post-hybridization washing and detection using the appropriate color fluorescent dyes. Microscopy is done using an Olympus Fluorescent microscope equipped with a computer assisted image analysis system and color wheel to chose the appropriate excitation wavelengths for each specific fluorescent dye (Perceptive Systems. Houston, Tex.).

Although the current invention has been described in connection with a specific form thereof, it is to be understood and appreciated that a wide array of equivalents may be substituted for the specific elements described and shown herein without departing from the spirit and scope of the invention as described in the appended claims.

LITERATURE CITED

Bhat, N. M., M. M. Bieber and N. N. H. Teng, "One Step Enrichment of Nucleated Red Blood Cells: a Potential Application in Prenatal Diagnosis," *Journal of Immunological Methods,* 158:277-280, 1993.

Bhat, N. M., M. M. Beiber, C. J. Chapman, F. K. Stevenson and N. N. H. Teng, "Human Anti-lipid A Monoclonal Antibodies Bind to Human B Cells and the I Antigen on the Cord Red Blood Cells," *Journal of Immunology,* 151: 5011-5021, 1993.

Bianchi, D. W., "Prenatal Diagnosis by Analysis of Fetal Cells in Maternal Blood," *Journal of Pediatrics,* 127:847-856.1995.

Cheung, M. C., J. D. Goldberg and Y. W. Kan, "Prenatal Diagnosis of Sickle Cell Anemia and Thalassemia by Fetal Cells in Maternal Blood," *Nature Genetics,* 14:264-268, 1996.

Halling, P. J., and P. Dunning, Enzyme *Microb. Technol.* 2:2-10 (1980)

Hirschbein. B. L., et al., *Chemtech,* March 1982: pp. 172-179

Phelan, J. P., M. O. Ahu, L. M. Korst and G. I. Martin, "Nucleated Red Blood Cells, a Marker for Asphyxia," *American Journal of Obstetrics and Gynecology,* 173: 1380-1384. 1993.

Simpson, J., L., D. E. Lewis, F. Z. Bisehoff and S. Elias, "Isolating Fetal Nucleated Red Blood Cells from Maternal Blood: the Baylor Experience—1995," *Prenatal Diagnosis,* 15:907-912, 1995.

Zhu, H. M., M. L. Lee and L. J. Sciorra, "Use of a Non-ionic Detergent (NP-40) to Generate Extended Chromatin for Fluorescence in Situ Hybridization Studies," *Applied Cytogenetics*, 20:125-128, 1994.

We claim:

1. A method of separating at least one target substance from at least one non-target substance in a sample containing a mixture of substances, which comprises:
   mixing the sample with a quantity of magnetic particles to produce a suspension comprising a magnetic component and a non-magnetic component, wherein the magnetic component comprises magnetic particles bound to the target substance through at least one moiety on the surface of the magnetic particles that directly or indirectly binds to the target substance, and the non-magnetic component comprises the remainder of the sample;
   placing the suspension onto a substrate material, wherein the substrate material comprises a viscous solution of agar, agarose, methylcellulose, or polyacrylamide that substantially prevents diffusion of the magnetic component unless a magnetic force is applied;
   exposing the substrate material containing the suspension to a magnetic field of sufficient strength to cause the magnetic component to migrate across the substrate material; and
   repeatedly applying a pre-determined increase in the magnetic field in a pulsing manner with a frequency sufficient to cause the magnetic component to separate spatially from the non-magnetic component of the suspension.

2. The method of claim 1 comprising the step of removing the magnetic component from the substrate material.

3. The method of claim 1 comprising the step of removing the magnetic particles from the target substance.

4. The method of claim 1 wherein the magnetic particles have uniform physical and magnetic properties.

5. The method of claim 1 wherein the magnetic particles are substantially identical.

6. The method according to claim 1 wherein the magnetic particles are beads.

7. The method according to claim 5 wherein the magnetic particles have a diameter from about 0.05 microns to about 4.5 microns.

8. The method of claim 1 wherein the magnetic particles are chosen from the group consisting of ferromagnetic, paramagnetic or superparamagnetic-particles.

9. The method of claim 8 wherein the magnetic particles are superparamagnetic particles.

10. The method of claim 1 wherein the magnetic particles include at least two different magnetic particles.

11. The method of claim 10 wherein the at least two different magnetic particles have different respective physical or electromagnetic properties.

12. The method of claim 1 wherein the moieties on the surface of the magnetic particles are ligands that directly bind to the target substance.

13. The method of claim 1 wherein the moieties on the surface of the magnetic particles are capture agents that bind to at least one ligand that binds to the target substance.

14. The method of claim 12 or 13, wherein the ligand binds to more than one target substance.

15. The method of claim 13, wherein the capture agent binds to more than one ligand.

16. The method of claim 12 or 13, wherein the ligands are selected from the group consisting of monoclonal antibodies and polyclonal antibodies.

17. The method of claim 1, wherein the sample comprises desired components and undesired components.

18. The method of claim 17, wherein the desired components are biological materials selected from the group consisting of eucaryotic cells, procaryotic cells, subcellular organelles, viruses, proteins, peptides, nucleic acids, lipids, carbohydrates, and complex molecules comprising a combination of at least two of nucleic acids, proteins, lipids and carbohydrates.

19. The method of claim 17, wherein the undesired components are biological materials selected from the group consisting of malignant cells, toxin-producing cells, bacteria, fungi, viruses, microbial parasites, proteins, peptides, and nucleic acids.

20. The method of claim 17, wherein the desired component is a specific cell type and the undesired components comprise other cell types present in the sample.

21. The method of claim 20, wherein the sample is derived from blood of a gestating female, and wherein the desired component comprises fetal cells disposed within the sample and the undesired component comprises maternal cells.

22. The method of claim 17, wherein the target substance is the desired component, and the non-target substance is an undesired component of the sample.

23. The method of claim 17, wherein the target substance is an undesired component of the sample, and the non-target substance is a desired component of the sample.

24. The method of claim 1 wherein the substrate material permits differential rates of migration between the magnetic component and the non-magnetic component.

25. The method of claim 1, wherein the methylcellulose is between about 1.7% and 2.0%.

26. The method of claim 1 wherein the substrate material is a growth media for growing at least one substance contained in the mixture.

27. The method of claim 1 wherein the step of placing the suspension onto a substrate material comprises placing the magnetic mixture along one edge of the substrate material.

28. The method of claim 1 comprising the step of labeling the target substance with a fluorescent marker.

29. The method of claim 1 comprising the step of labeling the non-target substance with a fluorescent marker.

30. The method of claim 1 wherein the magnetic field is of a strength of about 1.5 to about 2.0 Tesla.

31. The method of claim 1 wherein the magnetic field is of a strength of at least 3.0 Tesla.

32. The method of claim 1 wherein the frequency at which the magnetic field is activated and deactivated is from about 0.5 to about 10 seconds per pulse.

33. The method of claim 1 wherein the frequency at which the magnetic field is activated and deactivated is from about 1.0 to about 2.0 seconds per pulse.

34. The method of claim 1 wherein the frequency at which the magnetic field is activated and deactivated is about 2.0 seconds per pulse.

35. The method of claim 34 wherein the magnetic field strength varies substantially linearly with distance within a plane of the substrate material.

36. The method of claim 1 wherein the magnetic field has a strength that varies substantially linearly with distance.

37. The method of claim 1 wherein the activating and deactivating of the magnetic field is performed at a frequency such that the pulses overlap in time.

* * * * *